US012740712B2

(12) United States Patent
Kopelman et al.

(10) Patent No.: US 12,740,712 B2
(45) Date of Patent: Sep. 22, 2026

(54) SYSTEMS AND METHODS FOR IDENTIFYING AND CORRECTING FOOD TRAPS

(71) Applicant: ALIGN TECHNOLOGY, INC., San Jose, CA (US)

(72) Inventors: Avi Kopelman, Palo Alto, CA (US); Zelko Relic, Pleasanton, CA (US); Mitra Derakhshan, Herndon, VA (US)

(73) Assignee: Align Technology, Inc., San Jose, CA (US)

(*) Notice: Subject to any disclaimer, the term of this patent is extended or adjusted under 35 U.S.C. 154(b) by 166 days.

(21) Appl. No.: 18/656,338

(22) Filed: May 6, 2024

(65) Prior Publication Data

US 2024/0374144 A1 Nov. 14, 2024

Related U.S. Application Data

(60) Provisional application No. 63/500,815, filed on May 8, 2023.

(51) Int. Cl.

| | |
|---|---|
| ***A61B 5/00*** | (2006.01) |
| ***A61C 7/00*** | (2006.01) |
| ***A61C 9/00*** | (2006.01) |
| ***A61C 13/34*** | (2006.01) |

(52) U.S. Cl.

CPC ............ *A61B 5/0088* (2013.01); *A61C 7/002* (2013.01); *A61C 9/0053* (2013.01); *A61C 13/34* (2013.01)

(58) Field of Classification Search

CPC ......... A61B 5/0088; A61C 7/002; A61C 7/00; A61C 9/0053; A61C 9/0046; A61C 9/0066; A61C 13/28; A61C 13/30; A61C 13/34

See application file for complete search history.

(56) References Cited

U.S. PATENT DOCUMENTS

| | | | |
|---|---|---|---|
| 5,975,893 | A | 11/1999 | Chishti et al. |
| 6,099,314 | A | 8/2000 | Kopelman et al. |
| 6,309,215 | B1 | 10/2001 | Phan et al. |
| 6,334,772 | B1 | 1/2002 | Taub et al. |
| 6,334,853 | B1 | 1/2002 | Kopelman et al. |
| 6,450,807 | B1 | 9/2002 | Chishti et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,830,450 | B2 | 12/2004 | Knopp et al. |
| 6,845,175 | B2 | 1/2005 | Kopelman et al. |

(Continued)

*Primary Examiner* — Vijay Shankar

(74) *Attorney, Agent, or Firm* — FisherBroyles, LLP

(57) ABSTRACT

A system for treating food traps may include an intraoral scanner and a processor coupled in electronic communication with the intraoral scanner, a processor, and memory comprising instructions that when executed by the processor cause the system to carry out a method. The method may include receiving a 3D digital model of a patient's detention and analyzing the 3D digital model of the patient's detention by detecting anatomic structures in the 3D digital model of the patient's detention that correspond to food traps. The 3D digital model of the patient's detention may be displayed on a display and digital feedback may be provided on the displayed 3D digital model of the patient's detention. The feedback may identify a location of the food traps.

25 Claims, 21 Drawing Sheets

(56) References Cited

U.S. PATENT DOCUMENTS 6,979,196 B2 12/2005 Nikolskiy et al.
7,030,383 B2 4/2006 Babayoff et al.
7,202,466 B2 4/2007 Babayoff et al.
7,255,558 B2 8/2007 Babayoff et al.
7,286,954 B2 10/2007 Kopelman et al.
7,319,529 B2 1/2008 Babayoff
7,373,286 B2 5/2008 Nikolskiy et al.
7,507,088 B2 3/2009 Taub et al.
7,545,372 B2 6/2009 Kopelman et al.
7,698,068 B2 4/2010 Babayoff
7,916,911 B2 3/2011 Kaza et al.
8,108,189 B2 1/2012 Chelnokov et al.
8,244,028 B2 8/2012 Kuo et al.
8,587,582 B2 11/2013 Matov et al.
8,948,482 B2 2/2015 Levin
D742,518 S 11/2015 Barak et al.
9,192,305 B2 11/2015 Levin
9,261,356 B2 2/2016 Lampert et al.
9,261,358 B2 2/2016 Atiya et al.
9,299,192 B2 3/2016 Kopelman
D760,901 S 7/2016 Barak et al.
9,393,087 B2 7/2016 Moalem
9,408,679 B2 8/2016 Kopelman
9,431,887 B2 8/2016 Boltanski
9,439,568 B2 9/2016 Atiya et al.
9,451,873 B1 9/2016 Kopelman et al.
D768,861 S 10/2016 Barak et al.
D771,817 S 11/2016 Barak et al.
9,491,863 B2 11/2016 Boltanski
D774,193 S 12/2016 Makmel et al.
9,510,757 B2 12/2016 Kopelman et al.
9,660,418 B2 5/2017 Atiya et al.
9,668,829 B2 6/2017 Kopelman
9,675,430 B2 6/2017 Verker et al.
9,693,839 B2 7/2017 Atiya et al.
9,717,402 B2 8/2017 Lampert et al.
9,724,177 B2 8/2017 Levin
9,844,426 B2 12/2017 Atiya et al.
10,076,389 B2 9/2018 Wu et al.
10,098,714 B2 10/2018 Kuo
10,108,269 B2 10/2018 Sabina et al.
10,111,581 B2 10/2018 Makmel
10,111,714 B2 10/2018 Kopelman et al.
10,123,706 B2 11/2018 Elbaz et al.
10,136,972 B2 11/2018 Sabina et al.
10,195,006 B2 * 2/2019 Freiberg ................. A61C 17/00
10,380,212 B2 8/2019 Elbaz et al.
10,390,913 B2 8/2019 Sabina et al.
10,453,269 B2 10/2019 Furst
10,456,043 B2 10/2019 Atiya et al.
10,499,793 B2 12/2019 Ozerov et al.
10,504,386 B2 12/2019 Levin et al.
10,507,087 B2 12/2019 Elbaz et al.
10,517,482 B2 12/2019 Sato et al.
10,695,150 B2 6/2020 Kopelman et al.
10,708,574 B2 7/2020 Furst et al.
10,772,506 B2 9/2020 Atiya et al.
10,813,727 B2 10/2020 Sabina et al.
10,888,399 B2 1/2021 Kopelman et al.
10,952,816 B2 3/2021 Kopelman
10,980,613 B2 4/2021 Shanjani et al.
10,993,783 B2 * 5/2021 Wu .................... A61C 13/0004
11,013,581 B2 5/2021 Sabina et al.
D925,739 S 7/2021 Shalev et al.
11,096,765 B2 8/2021 Atiya et al.
11,238,586 B2 2/2022 Minchenkov et al.
11,367,192 B2 6/2022 Kopelman et al.
11,455,727 B2 9/2022 Minchenkov et al.
11,478,132 B2 10/2022 Kopelman et al.
11,563,929 B2 1/2023 Saphier et al.
11,564,777 B2 * 1/2023 Kopelman ............. A61C 7/023
11,633,268 B2 4/2023 Moalem et al.
11,707,238 B2 7/2023 Moshe et al.
RE49,605 E 8/2023 Kopelman
11,744,681 B2 9/2023 Kopelman et al.
11,759,277 B2 9/2023 Shalev et al.
11,801,126 B2 * 10/2023 Hansen .............. A61C 13/0004
11,896,461 B2 2/2024 Saphier et al.
11,937,996 B2 3/2024 Peleg
11,995,839 B2 5/2024 Weiss et al.
12,370,015 B2 * 7/2025 Winchell ............... B33Y 80/00
2018/0153649 A1 * 6/2018 Wu ........................ A61C 7/002
2019/0083208 A1 * 3/2019 Hansen .................... A61C 5/88
2021/0121049 A1 4/2021 Rudnitsky et al.
2021/0137653 A1 5/2021 Saphier et al.
2021/0196152 A1 7/2021 Saphier et al.
2022/0039917 A1 * 2/2022 Winchell ............... B33Y 10/00
2023/0030704 A1 * 2/2023 Weinstein ................ A61C 7/14

* cited by examiner

SYSTEMS AND METHODS FOR IDENTIFYING AND CORRECTING FOOD TRAPS

RELATED APPLICATIONS

This application claims the benefit under 35 U.S.C. § 119 (c) of U.S. Provisional Patent Application No. 63/500,815, filed May 8, 2023, and titled "SYSTEMS AND METHODS FOR IDENTIFYING AND CORRECTING FOOD TRAPS," which is incorporated, in its entirety, by this reference.

BACKGROUND

A food trap is a small space or gap in or between teeth where food particles can become lodged or trapped after eating. These areas can be created by various factors such as misaligned teeth, dental restorations that don't fit properly, gaps resulting from tooth loss or extraction, carries, or other dental defects.

If not treated, food traps can lead to several problems including plaque buildup, wherein trapped food particles can mix with bacteria and saliva, forming plaque. Over time, the buildup of plaque can lead to dental issues such as carries, also referred to as cavities, and tooth decay. Food traps can also lead to the accumulation of bacteria and plaque around the trapped food which can irritate the gums, leading to gingivitis or periodontal disease. If left untreated, gum disease can cause tooth loss and may damage the underlying bone structure. Decomposing food particles and bacteria can produce foul odors, leading to persistent bad breath, also referred to as halitosis. Prolonged exposure to trapped food particles and bacteria can erode the tooth enamel, resulting in cavities and tooth decay.

Prior detection and treatment of food traps were less than ideal in many ways. For example, detection of food traps relies on patient's noticing food traps and then remembering to report them to their dentist. Treatment involved manually addressing by encouraging proper oral hygiene practices like brushing and flossing.

The methods and apparatuses described herein may improve food trap detection, prevention, and treatment, including automated detection, evaluation of treatment options, and treatment, which may result in increased patient dental health and dental outcomes.

SUMMARY

As will be described in greater detail below, the present disclosure describes various systems and methods for detection, prediction, and treatment of food traps.

In addition, the systems and methods described herein may improve the functioning of a computing device by reducing computing resources and overhead for detecting and predicting formation of food traps and may improve the quality of dental treatment, thereby improving processing efficiency of the computing device and resulting improved dental outcomes over conventional approaches. These systems and methods may also improve the field of orthodontic treatment by improving food trap detection and predictability of treatment.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Figure 1:
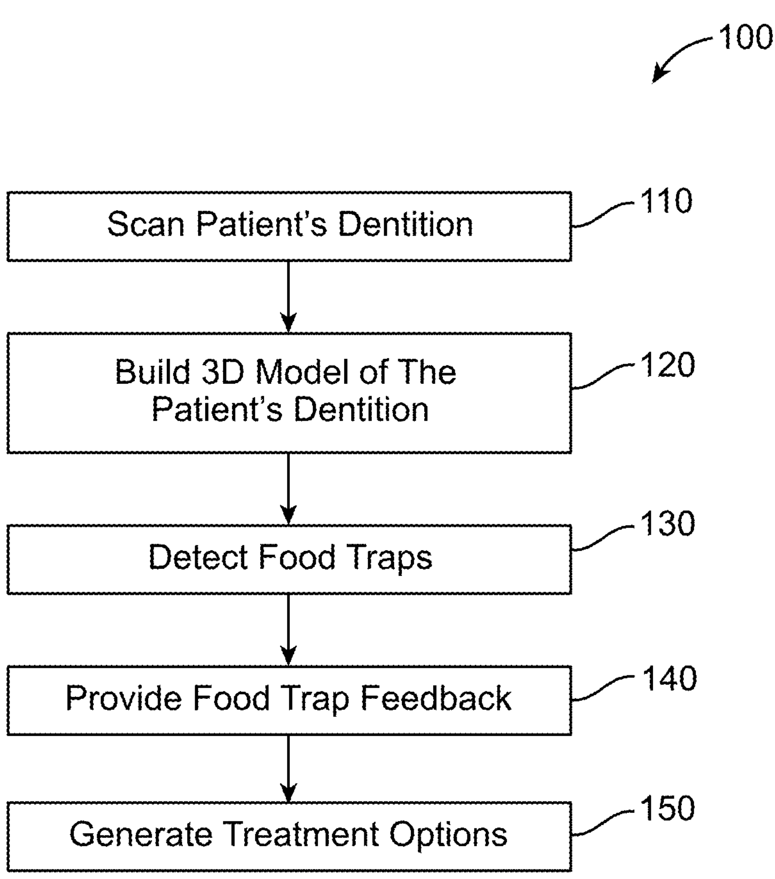
FIG. 1 illustrates an exemplary method of detecting food traps, in accordance with some embodiments.

FIG. 1 illustrates an exemplary method of detecting food traps. The method 100 may include scanning a patient's detention to generate scan data which may include 2D and/or 3D data representing the surface and internal structures of the patient's detention, building a model or models, including a 3D surface model and/or subsurface and volumetric model of the patient's detention based on the scan data, using the scan data and the model(s) to detect the presence of food traps, provide food trap feedback, such as an indication of the location of the possible presence of a food trap or a predicted development of a food trap, and generate treatment options for treating existing food traps or avoid development of food traps, such as through orthodontic treatment.

The method of detecting food traps 100 may begin at block 110, which includes scanning a patent's dentition. The patient's dentition may include the tissue and anatomy within the intraoral cavity of the patient, including the patient's teeth, gingiva, jaw bones, and intraoral surfaces of the checks, and lips.

Scanning may include 2D scanning, such as the capture of 2D color images of the surfaces of the patient's dentition, such as the surfaces of the teeth, gingiva, and intraoral surfaces of the checks, and lips. An intraoral scanner may include a color imaging sensor and optics for recording color data during an intraoral scan of the patient. The color data may be corelated with a location in the intraoral cavity to aid in combining the 2D color data with other data captured during an intraoral scan or data of the patient's dentition captured using other systems and methods.

Scanning may also include 3D surface scanning of the patient's dentition, including the intraoral surfaces of the teeth, gingiva, and intraoral surfaces of the cheeks, and lips. An intraoral scanner may include an imaging sensor and optics for recording 3D data during an intraoral scan of the patient. The 3D data may be point cloud data that is registered together to form a 3D surface model of the patient's dentition. The 3D data may be combined with the 2D color data to create a color 3D surface model of the patient's dentition and/or with other data captured during an intraoral scan or data of the patient's dentition captured using other systems and methods.

Scanning may also include near-infrared scanning of the patient's dentition, including the teeth, gingiva, jaw bones, the checks, and lips. An intraoral scanner may to record near-infrared light and optics for recording near-infrared data during an intraoral scan of the patient.

Near infrared light may penetrate the tissues and anatomy of the patient's intraoral cavity. Near infrared scan data may include data related to the subsurface and internal structures of the patient's anatomy, such as tooth caries, jaw bone structure, tooth root position, and shape, gingiva defects, and other internal structures of the patient's anatomy. The near-infrared data may be combined with the 3D data and/or 2D data to add volumetric data to, for example, a 3D surface model of the patient's dentition and/or with other data captured during an intraoral scan or data of the patient's dentition captured using other systems and methods. Combining the 3D surface data with the near-infrared data may include generated a volumetric 3D model of the patient's dentition.

A surface model may include data related to the location, shape, and color of the external surfaces of the patient's dentition. While a 3D surface model may define a volume, it may not have information related to the internal structures within the volume. A volumetric 3D model may include subsurface data and may include information related to the internal structures within a volume defined by the 3D surface data or below the surfaces captured by the 3D scan. An example of near-infrared scan data is provide in FIG. 2I.

Scanning may also include cone-beam computed tomography (CBCT) scanning of the patient's dentition, including the teeth, gingiva, jaw bones, the checks, and lips. CBCT scanning is an advanced dental imaging technique that uses a cone shaped X-ray beam to generate three-dimensional (3D) images of a patient's teeth, jaws, and surrounding structures. During a CBCT scan, the X-ray source and detector rotate around the patient's head, capturing multiple images from various angles. These images are then processed to create a single 3D representation of the area of interest or the patient's dental tissues including teeth, jaws, neck and even cars, nose, and throat.

The 3D data generated by a CBCT scan may be combined with the 3D surface data, color data, and/or near-infrared scan data to generate a 3D volumetric model of the patient's detention.

At block 120, a model of the patient's detention may be built. In some embodiments, the model may be built at block 110, such as simultaneously with one or more of the scanning processes described above. The model or models generated through scanning or generated later based on the scan data may be evaluated for the existence of food traps. In some emblements, a single model may be generated from a multi-modal 3D intraoral scanner that generates 3D surface data and subsurface data. The single model may combine aspects of the 3D data, such as 3D surface data, color data, near-infrared data, and the CBCT data. In some embodiments, the scan data, including the 3D scan data, the 2D scan data, the Near-infrared scan data, and the CBCT scan data may not be combined in a single model and may instead be separately stored and evaluated for the existence of food traps.

At block 130 food traps may be detected based on the scan data. The detection of food traps may be made based on a evaluation or analysis of the scan data. The evaluation or analysis may be carried out in many ways. For example, the position and shape of the patient's teeth may be analyzed based on the 3D surface data. The size and shape of the interproximal region and the angles of the teeth may be extracted from the 3D data to determine if the shape has the qualities of a food trap. Food may be detected in the 3D data or the color data. The existence of food in the patient's detention may indicate the existence of a food trap at that location. A machine learning or artificial intelligence algorithm may be trained based on images and 3D and other scan data tagged with the location of food traps. The trained algorithm may then evaluate the patient's scan data to determine the existence of food traps. FIGS. 2A-2J and the associated text herein, describe the structures and features that may be detected and may indicated the existence of a food trap. At block 130, the structures of the dentition shown and described with respect to FIGS. 2A-2J may be detected.

Figure 2A:
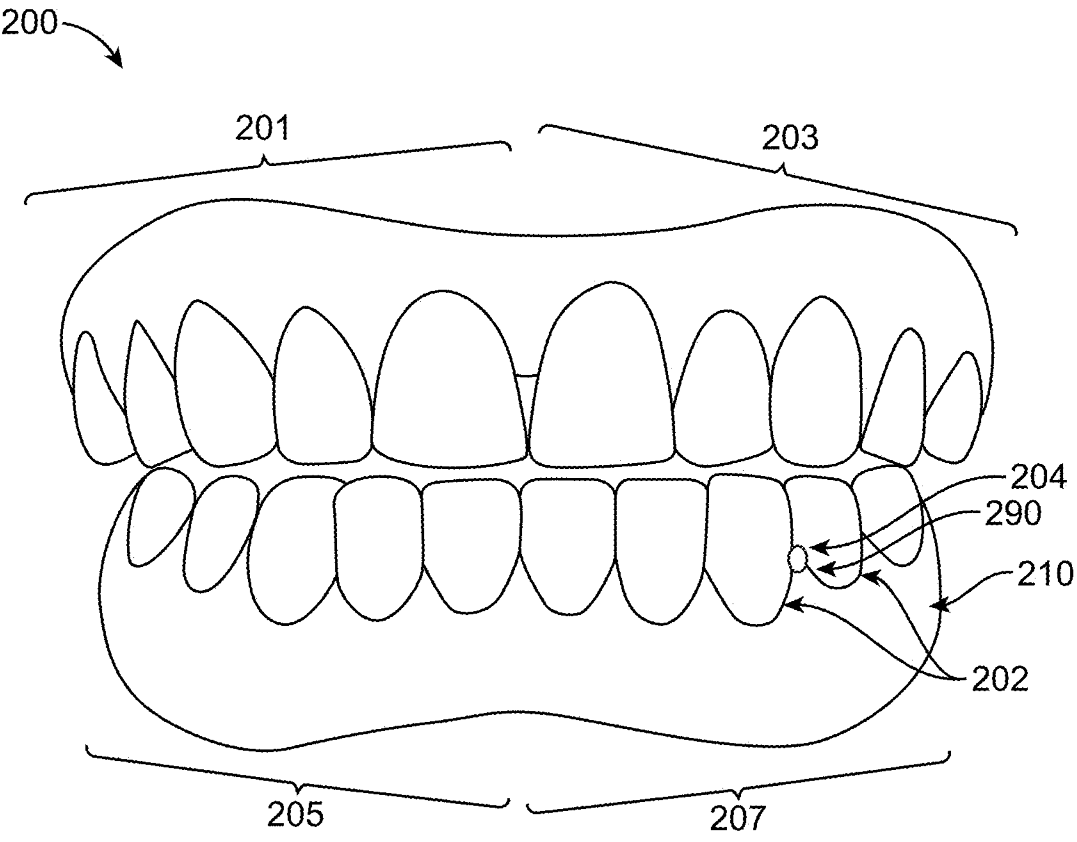
FIG. 2A illustrates food captured in a food trap in a patient's dentition, in accordance with some embodiments.

With reference to FIG. 2A illustrates food captured in a food trap in a patient's dentition. A patient's dentition my include the oral cavity and the anatomy therein. Adult's typically have 32 permanent teeth 202, which may be divided into four quadrants: maxillary left 201, maxillary right 203, mandibular left 205, and mandibular right 207. Each quadrant may include eight teeth including two incisors, one canine, two premolars, and two or three molars. The incisors are the anterior (front) teeth located, used for biting and cutting food, while the canines are sharp and pointed, used for tearing and shredding. The premolars and molars are located towards the back of the mouth and are used for chewing and grinding food.

Figure 2B:
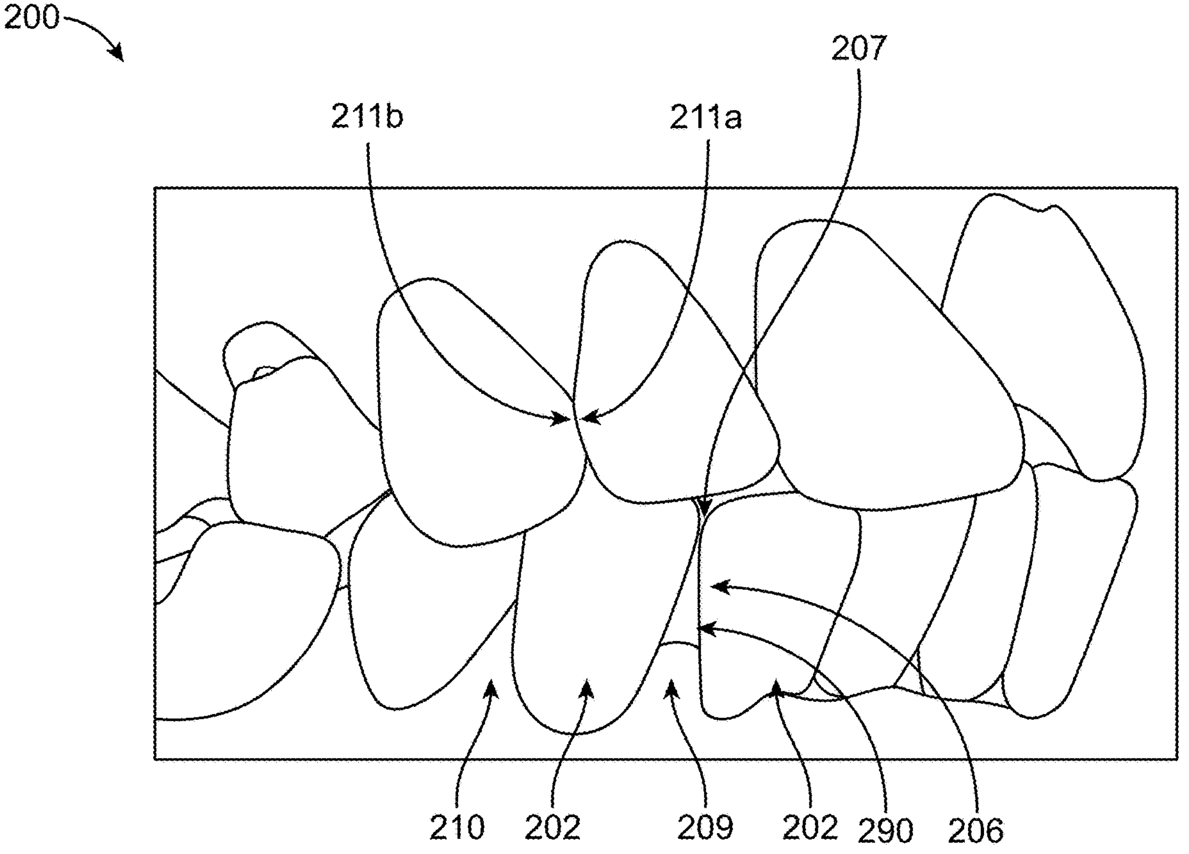
FIG. 2B illustrates interproximal and vestibule food traps in a patient's dentition, in accordance with embodiments.
Figure 2C:
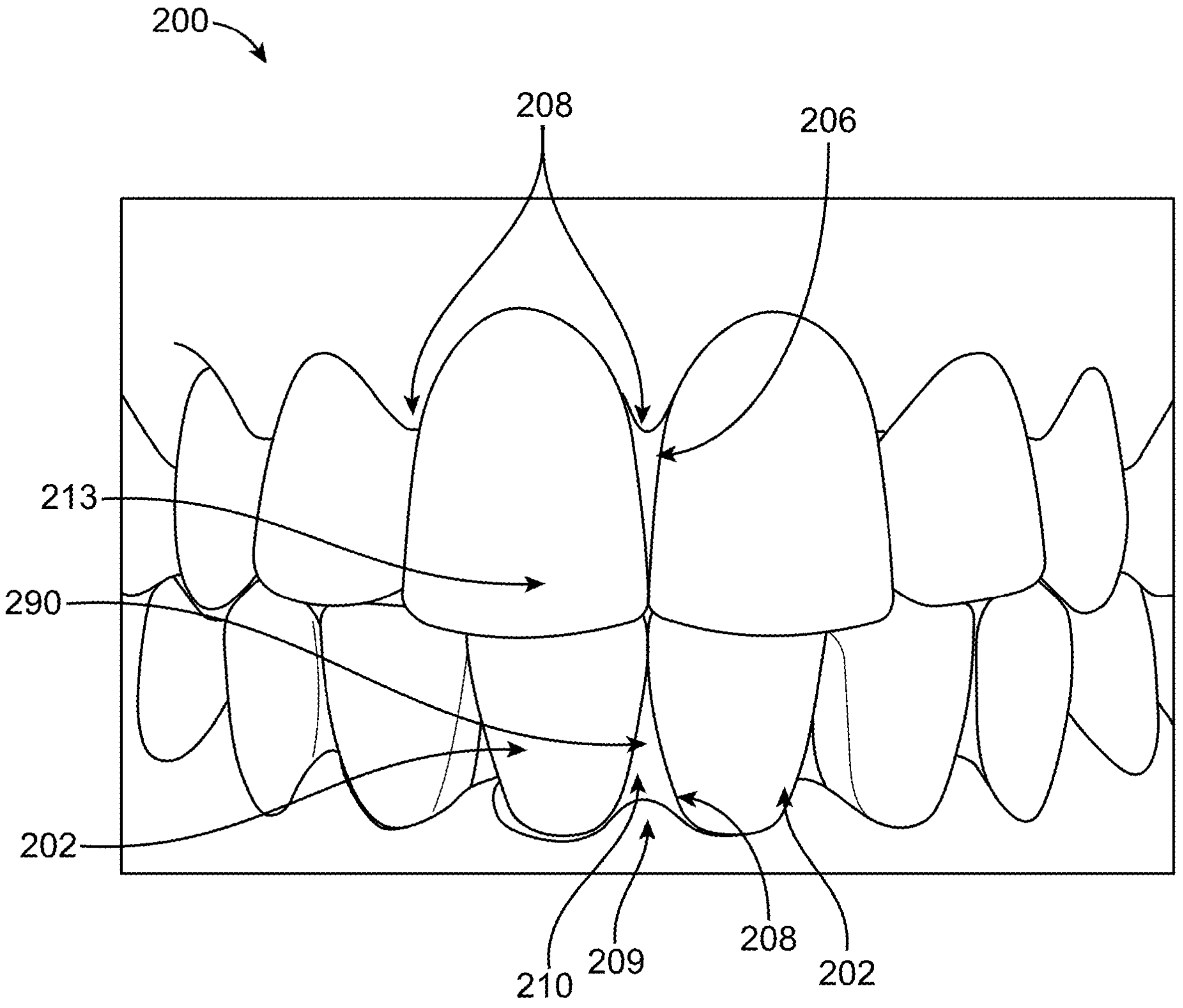
FIG. 2C illustrates black triangle food traps in a patient's dentition, in accordance with embodiments.
Figure 2D:
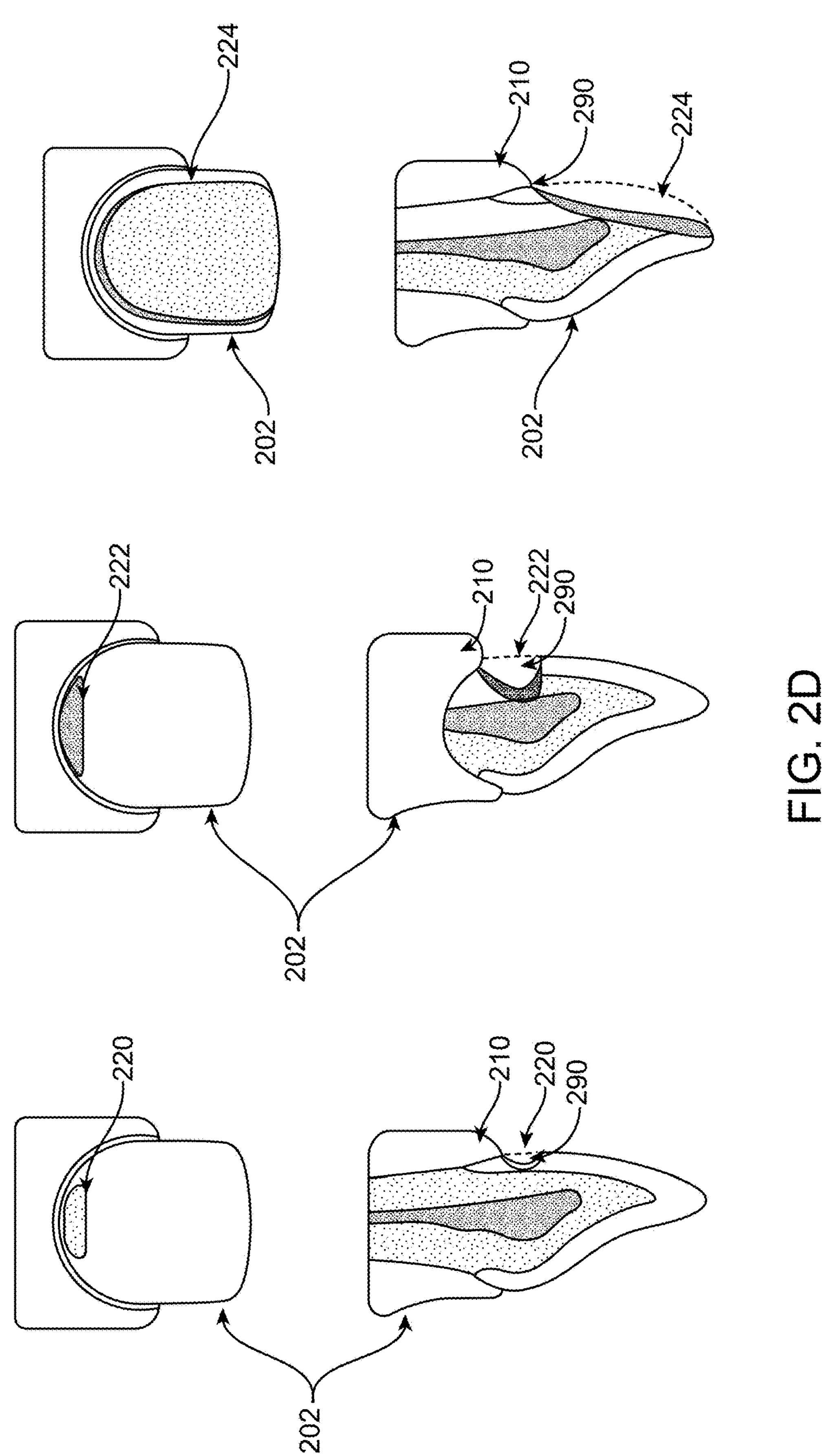
FIG. 2D illustrates abrasion, abfraction, and erosion food traps in a patient's dentition, in accordance with embodiments.
Figure 2E:
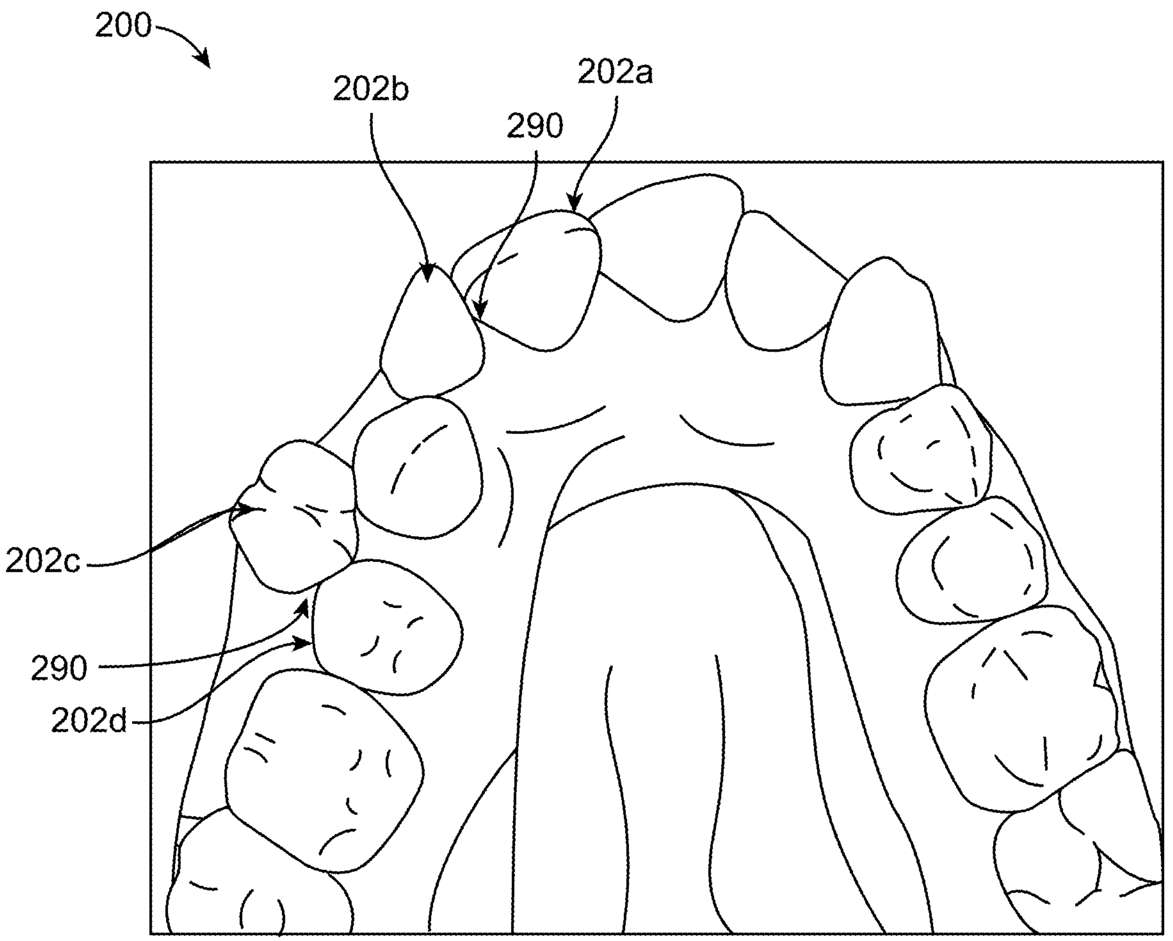
FIG. 2E illustrates food traps caused by overlapping teeth in a patient's dentition, in accordance with embodiments.
Figure 2F:
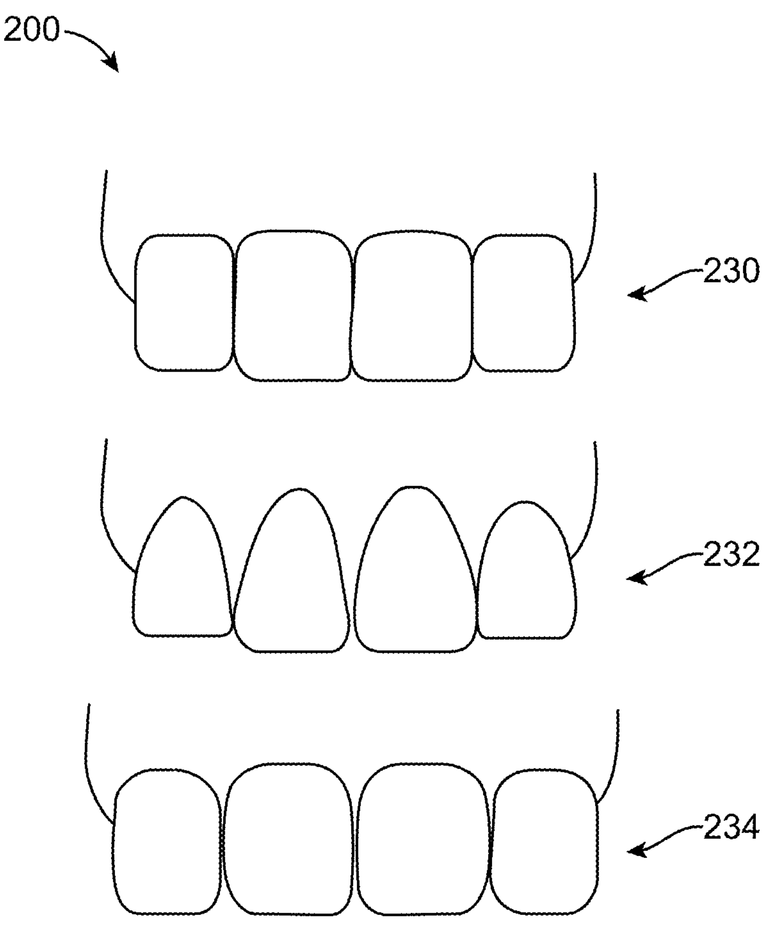
FIG. 2F illustrates tooth morphology types that may lead to food traps, in accordance with embodiments.
Figure 2G:
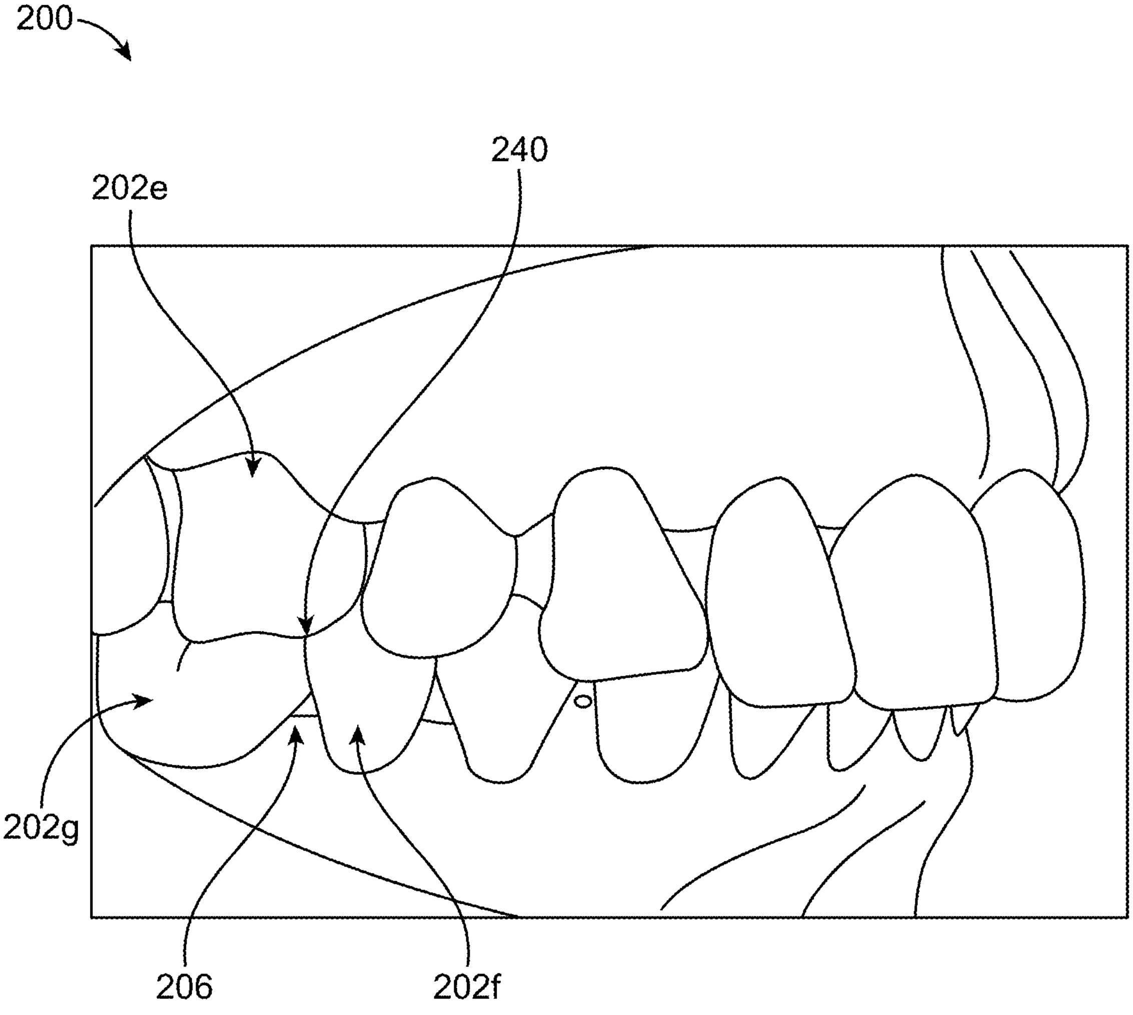
FIG. 2G illustrates how bite contacts and tooth mobility in a patient's dentition can create food traps, in accordance with embodiments.
Figure 2H:
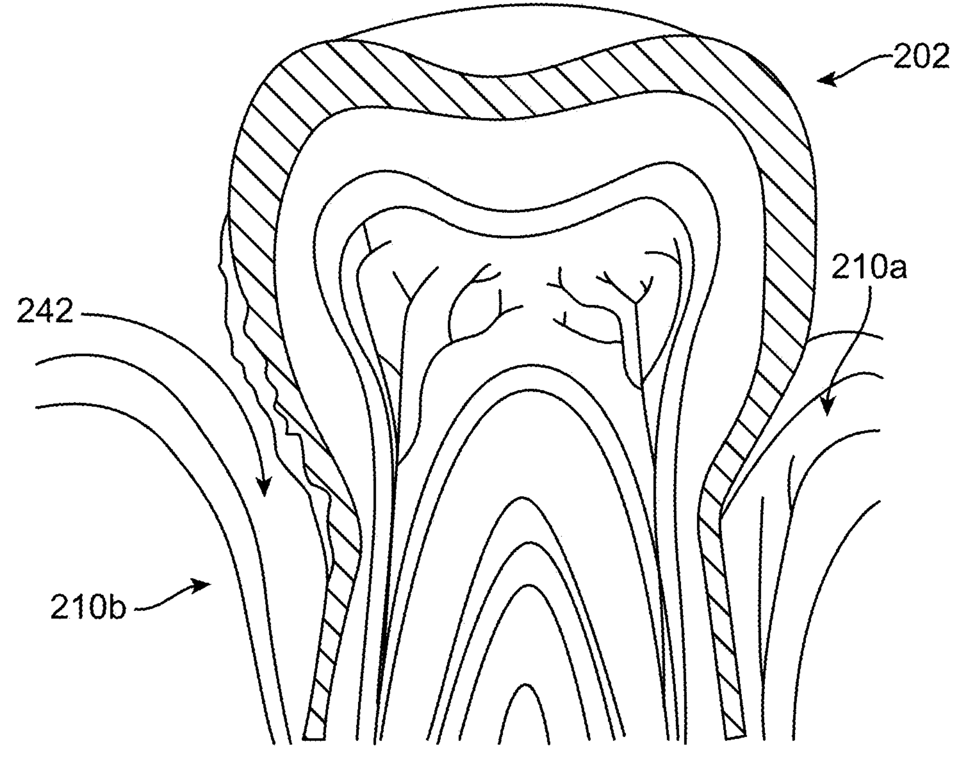
FIG. 2H illustrates near-infrared scanning in the detection of food traps in a patient's detention, in accordance with embodiments.
Figure 2I:
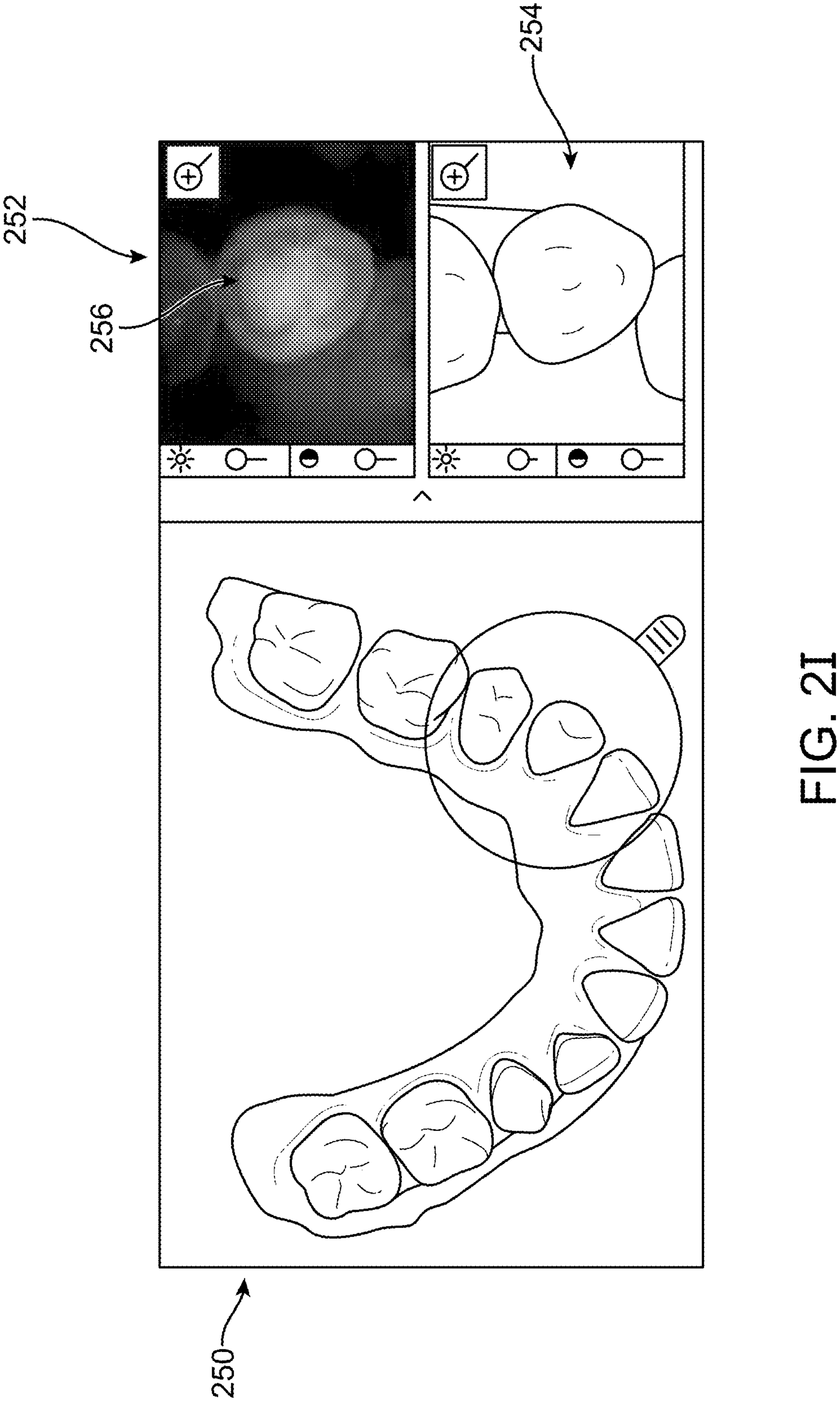
FIG. 2I illustrates near-infrared scanning in the detection of food traps in a patient's detention, in accordance with embodiments.
Figure 2J:
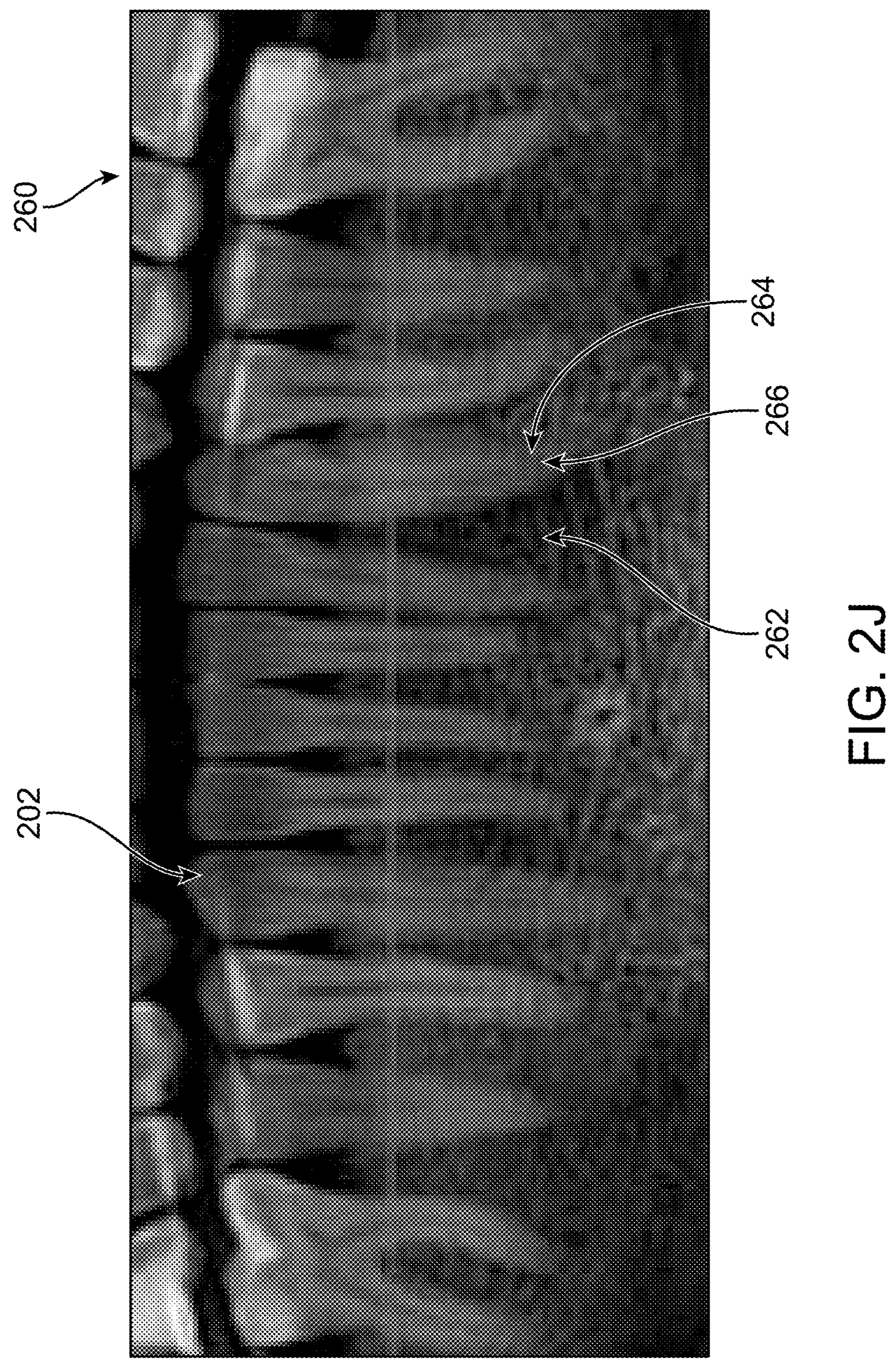
FIG. 2J illustrates cone-beam computed tomography (CBCT) scanning in the detection of food traps in a patient's detention, in accordance with embodiments.

The teeth 202 are anchored into the jawbone (maxilla and mandibula) by roots 266 (see, FIG. 2J), which are covered by periodontal ligament and surrounded by alveolar bone 262 (see, FIG. 2J). The dentition also includes the surrounding soft tissues, such as the gingiva (gums) 210, tongue, and buccal mucosa (checks).

The dentition 200 includes two adjacent teeth 202 with food 204 stuck in and interproximal region between the two adjacent teeth 202. The food 204 is stuck in what may be referred to as a food trap 290. A food trap 290 may be space or gap between teeth or in other locations within the patient's oral cavity where food particles can become lodged or trapped after eating. Food traps 290 can be created by various factors such as misaligned teeth, dental restorations that don't fit properly, poor gum health, or gaps resulting from tooth loss or extraction.

Poorly fitted crowns, bridges, or fillings can create gaps, and other issues with dental restorations, such as dental implants can lead to food traps. Even properly fitted restorations may lead create food traps. Sometimes, tooth loss or extraction, such as when a tooth is lost or removed, the surrounding teeth can shift, creating gaps and spaces where food can become trapped. Other dental issues may also lead to food traps, for example, buildup of plaque can lead to tooth decay and eventual tooth carries which may form cavities that trapped food. Sometimes, the accumulation of bacteria and plaque on the patient's dentition make irritate the gums leading to gingivitis or periodontal disease.

In some embodiments the gum or gingiva may recede creating pockets or space and interproximal areas between the teeth or between the gingiva and a tooth root which may trapped food. Tooth damage, caused by abrasion and fraction or erosion may also lead to pockets within the teeth or between the teeth and the gingiva may cause food traps. These and other potential food traps are discussed herein below with respect to FIGS. 2A-2J.

FIG. 2B illustrates interproximal and vestibule food traps in a patient's dentition. The interproximal area 206, also known as the interdental or proximal area, refers to the space or region between two adjacent teeth 202 in the dental arch 200. This area plays a role in oral hygiene, dental restorations, and orthodontics, as it is where teeth are in close contact. Dental problems in the interproximal region can affect patient health.

The interproximal area 206 may include several features including the contact point 207. The contact point 207 is the location on the adjacent tooth crowns where the surfaces of two adjacent 202 teeth touch each other. It is generally located near the middle third of the tooth crown. The contact points help stabilize the dental arch and properly located contact points 207 may aid in preventing food impaction between teeth during chewing and food getting stuck in a food trap.

The interdental papilla 209 is the small, triangular-shaped piece of gingival tissue that fills the space between adjacent teeth at the lower or gingival location of the crown. The interdental papilla 209 helps support the teeth and protects the underlying bone and periodontal ligament The interdental papilla also plays a in maintaining periodontal health and preventing food impaction.

The proximal surfaces 211 are the tooth surfaces that face each other in the interproximal area. The proximal surfaces 211 are typically referred to as the mesial proximal surface 211*a*, the surface closest to the midline of the dental arch, and the distal proximal surface 211*b*, the surface farthest from the midline.

The interproximal space 206 is the area, space, or volume between the proximal surfaces of adjacent teeth, extending from the contact point 207, if any, to the gingiva 210, such as the interdental papilla 209.

A food trap 290 may be formed within the interproximal area between two adjacent teeth. For example, a food trap may be formed between the contact point 207, the proximal surfaces 211, and the gingiva 210. In some embodiments, the food trap 209 may form in the product interproximal area 206 even when the two adjacent teeth 202 do not contact. In some embodiments, the food trap may extend from the lingual side of the teeth to the buccal side of the teeth.

In some embodiments, the food trap may be located in the vestibule area of the interproximal area where the food is trapped on a lingual or buccal side of the patient's teeth in the interproximal area 210 without extending through to the opposite side of the teeth.

FIG. 2C illustrates black triangle food traps in a patient's dentition. Black triangles 208, also known as open gingival embrasures, are triangular-shaped spaces that appear in the interproximal area 206 between the teeth near the gum line. Black triangles 208 occur when the papilla 208, the small triangular piece of gingiva 208 (also referred to as gum tissue) between the teeth, recedes or fails to fill the interproximal area 206 between the two adjacent teeth 202 completely through a hole or aperture 213 formed between the teeth. As a result, the dark background of the oral cavity becomes visible through the aperture 213, giving the appearance of black triangles between the teeth. Black triangles are not only an aesthetic concern but can also lead to functional problems, such as food traps and increased plaque accumulation.

Several factors can contribute to the formation of black triangles, including periodontal disease caused or gingivitis can cause inflammation, leading to gum recession and the loss of papillary height, which may result in black triangles. Tooth movement, such as from orthodontic treatment, natural tooth shifting, or misalignment can create spaces between teeth where the papilla does not completely fill the gap, forming a black triangle. Bone loss due to the loss of underlying bone support due to periodontal disease, aging, or trauma can contribute to gum recession, tooth movement, tooth mobility, and the formation of black triangles. Tooth shape or size may also contribute to black triangles. Some teeth may have a naturally tapered shape towards the gum line, making it difficult for the papilla to fill the entire space, creating black triangles.

Treatment options for black triangles may involve a combination of periodontal therapy, orthodontic treatment, or dental restorations like veneers or bonding to reshape the teeth and close the spaces. In some cases, a periodontist may perform a procedure known as papilla regeneration to restore the lost gum tissue and fill the black triangle.

FIG. 2D illustrates abrasion, abfraction, and erosion food traps in a patient's dentition. Pathological wearing away of tooth structure caused by mechanical forces other than normal tooth-to-tooth contact may be referred to as tooth abrasion. The abrasion process results in the loss of tooth enamel and, in some cases, dentin, leading to a variety of dental issues, such as tooth sensitivity, increased risk of decay, and changes in tooth shape, or appearance and may lead to the formation of an abrasion recess 220 within a tooth 202. The abrasion recess 220 may form a food trap 290 that catches and retrains food.

Tooth abrasion may be caused by improper or aggressive tooth brushing techniques, using a toothbrush with hard bristles, or abrasive toothpaste. The excessive force and abrasive materials can gradually wear away the tooth enamel, particularly at the gumline, where the tooth structure is thinner. Over time, the abrasive force and wears away of the tooth enamel can create V-shaped or U-shaped notches or grooves that for abrasions 220, which can expose the underlying dentin layer and make the teeth more susceptible to sensitivity, decay, and trapping food. Other factors contributing to tooth abrasion may include foreign objects such as toothpicks, dental floss, or even oral piercings that repeatedly come into contact with the teeth. In some cases, occupational exposure to abrasive materials, such as sand or metal particles, can also lead to tooth abrasion.

Dental professionals may treat tooth abrasions in many ways, such as by using dental bonding, veneers, or crowns to restore the affected tooth's structure, function, and appearance.

Tooth abfraction refers to the loss of tooth structure, such as enamel, near the gumline, such as represented by the tooth abfraction 222 in tooth 202. An abfraction may be caused by biomechanical forces, such as excessive occlusal (biting) forces or tooth flexion. Unlike abrasion, which involves wear caused by external mechanical factors, abfraction is thought to result from repeated stress and strain on the tooth structure, leading to microfractures and eventual loss of enamel and dentin. Thea abfraction may catch and trap food, forming a food trap 290.

A tooth abfraction may be caused by bruxism, the habit of clenching or grinding teeth, especially during sleep, which can create large occlusal forces on the teeth, leading to tooth flexion and abfraction lesions. Misaligned teeth or an improper bite can result in uneven distribution of occlusal forces, causing stress on certain teeth and contributing to abfraction. Parafunctional habits, such as nail-biting or pen-chewing can apply additional stress on teeth, increasing the risk of abfraction.

Abfraction lesions typically appear as wedge-shaped or V-shaped notches near the gumline, which can expose the underlying dentin and lead to tooth sensitivity, increased risk of decay, esthetic concerns, and food traps 290.

Treatment for tooth abfraction may include orthodontic therapy to correct high occlusion forces due to malocclusion of the patient's detention, an occlusal splint for bruxism to help redistribute occlusal forces and protect teeth from further damage. Restorative procedures such as dental bonding, veneers, or crowns may be used to restore the tooth's structure, function, and appearance.

Tooth erosion refers to the progressive loss of tooth structure, specifically the enamel, due to chemical dissolution by acids not caused by bacteria. Unlike tooth abrasion and abfraction, which involve mechanical wear, tooth erosion results from chemical processes. Tooth erosion can lead to a range of dental issues, such as tooth sensitivity, increased risk of decay, changes in tooth shape, esthetic concerns and food traps 290. A food trap may form between an eroded tooth and the gingiva 210 or in cavities or recesses formed by the eroded tooth.

Tooth erosion may be cased by many factors, including, frequent consumption of acidic foods and beverages, such as citrus fruits, soft drinks, and fruit juices, can expose teeth to acids that demineralize the enamel over time. Gastroesophageal reflux disease or acid reflux may cause stomach acids to flow back into the mouth, exposing teeth to erosive gastric acids and eroding teeth. Reduced saliva production or xerostomia can lead to an acidic oral environment, increasing the risk of tooth erosion and some medications, such as aspirin or vitamin C supplements, can be acidic and contribute to tooth erosion if held in the mouth or chewed.

Tooth erosion may be mitigated by treating the underlying causes, such as by managing or resolving GERD, eating disorders, or xerostomia to reduce the risk of further tooth erosion, modifying a patient's diet to limit the consumption of acidic foods and beverages, minimizing contact between acidic drinks and teeth, and by rinsing the mouth with water after consuming acidic substances. Fluoride treatments or the use of fluoride toothpaste can help strengthen and remineralize tooth enamel, reducing the risk of erosion.

In cases of severe erosion, restorative procedures, such as dental bonding, veneers, or crowns may be used to restore the tooth's structure, function, and appearance.

FIG. 2E illustrates food traps caused by overlapping teeth in a patient's dentition. Overlapping teeth, known as dental crowding, is a type of malocclusion that may occur when one or more teeth 202 grow or shift out of their proper alignment, partially covering the adjacent teeth. Overlapping teeth may be caused by crowding. Tooth crowding may be due to limited space in the dental arch. Teeth may be forced to overlap, twist, or rotate, resulting in an irregular and misaligned appearance. In some embodiments, one tooth may protrude in front of or sit behind the neighboring tooth, partially covering it.

The dentition 200 in FIG. 2E depicts multiple pieces of overlapping teeth due to tooth crowding. For example, tooth 202A and tooth 202B are overlapping due to tooth crap. Tooth 202B has rotated and been pushed in front of tooth 202A. The crowding between tooth 202B and tooth 202B may cause the formation of a food trap 290 in the location of the overlap between the two teeth. Unlike food traps formed in the interproximal region, food traps formed by tooth crowding occur between two teeth but in some embodiments may not form in the interproximal region. For example, the food trap 990 may be formed between a lingual surface of tooth 202B and a distal surface 290 of tooth 202A.

Another example of a food trap 290 is depicted between tooth 202C and 202D. Tooth 202C may have been pushed in a buccal direction by crowding of the dentition. Tooth 202D may have closed the gap formed by the buccal movement of tooth 202C. The food trap 290 may formed between the lingual surface of tooth 202C and the buccal surface of tooth 202D.

Overlapping teeth can be caused by various factors, including genetic predisposition, jaw size, tooth size, early or late loss of primary teeth, and habits like thumb sucking or tongue thrusting. Overlapping teeth can lead to several oral health issues, such as difficulty in maintaining proper oral hygiene, increased risk of tooth decay and gum disease, uneven wear on the teeth, and potential bite problems or jaw pain, and food traps which may accelerate tooth decay, gum disease, and etc.

Orthodontic treatment may be used to treat overlapping teeth. In some cases, tooth extraction or dental surgery may be used to create space and allow for proper alignment of the remaining teeth.

The FIG. 2F illustrates tooth morphology types that may lead to food traps. Tooth morphology refers to the study of the shape, size, structure, and arrangement of teeth within the dental arch. Tooth morphology and analysis of teeth with respect to tooth morphology may be used to identify, diagnose, and treat various dental conditions, as well as carry out restorative and cosmetic dental procedures.

Tooth morphology also encompasses other aspects such as the arrangement and number of teeth, the patterns of cusps and grooves on the tooth surface, and the structure of the enamel, dentin, and pulp within the tooth. Tooth morphology may be a consideration in identifying and addressing various dental issues, design effective dental appliances and restorations, and provide tailored dental care based on an individual's unique dental anatomy. Tooth morphology may also play a role in the development or treatment of food traps. As an example, differently shaped incisors may play a role in the development and treatment of food traps.

FIG. 2F depicts teeth 230 with a rectangular morphology, teeth 232 with a triangular morphology, and teeth 234 with a barrel morphology. Rectangular teeth 230 have a generally rectangular shape when viewed buccally (such as from the front of the incisors). Teeth with a rectangular morphology may be less prone to developing food traps in the interproximal region due to the close-fitting nature between the sides of adjacent teeth. Triangular teeth 232 of a generally triangular shape when viewed buccally such as from the front of the incisors). The triangle shape may include a wide incisal or occlusal surface and then a taper to a more narrow width at the gingiva.

Triangular teeth 232 may be more susceptible to the creation of food traps due to the wider distance in the interproximal area between adjacent teeth. Food traps developed in the interproximal area between adjacent teeth and retreated by, for example, interproximal reduction of the teeth to narrow the teeth and reduce the triangular area of the teeth and then through orthodontic treatment to close the interproximal gab crated by the interproximal reduction.

Barrel shape teeth 234 may be intermediately susceptible to the creation of food traps due to the wider distance in the interproximal area between adjacent teeth as compared to teeth with a rectangular morphology but narrower distance in the interproximal area between adjacent teeth as compared to teeth with a triangular morphology. Food traps developed in the interproximal area between adjacent teeth and retreated by, for example, interproximal reduction of the teeth to narrow the teeth and reduce the triangular area of the teeth and then through orthodontic treatment to close the interproximal gab crated by the interproximal reduction.

Other aspects of tooth morphology may also play a role in the development of food traps. Excessive wear on the chewing surfaces of teeth due to bruxism (teeth grinding), acid erosion, or abrasive tooth brushing can cause a loss of tooth structure, sensitivity, or altered tooth shape which may lead to tooth shapes that are susceptible to capturing and retaining food.

Fractured or chipped teeth caused by trauma, decay, or biting on hard objects can lead to fractures or chips in the tooth, affecting the tooth's function, integrity, and appearance. Fractures or chips in the patient's two may lead to the creation of food traps.

Tooth shape abnormalities, which may be caused by genetic factors or developmental issues can lead to abnormally shaped teeth, such as peg-shaped or fused teeth, which can impact the aesthetics and functionality of the teeth including the formation of food traps.

Some teeth may have deep grooves or pits on the chewing surfaces, making them more susceptible to catching and retaining food causing plaque accumulation and tooth decay.

FIG. 2G illustrates how bite contacts and tooth mobility in a patient's dentition can create food traps. Bite contacts between opposing arches refer to the points where upper and lower teeth meet when the jaws are closed. While these contacts aid in the normal chewing and mastication function of the teeth and jaw, in some embodiments, they may contribute to food getting stuck in teeth and food traps. For example, in some embodiments, misaligned contacts contacts between the upper and lower teeth are due to malocclusion may cause the teeth may not fit together properly when biting down. This misalignment can push food into small gaps or spaces, such as food traps, between teeth.

In some embodiments, excessive tooth wear, erosion, or dental restorations may result in uneven tooth surfaces, causing food traps. When opposing arches come into contact, food may be pushed into these irregularities become lodged. Similarly, in some embodiments, some teeth, particularly molars, may have deep grooves or pits on their chewing surfaces. When the jaws close, and the teeth of the opposing arches come into contact, food particles can become trapped within food traps created by these grooves or pits.

Improper intercuspation, the way cusps (the raised points on the chewing surfaces of teeth) of teeth of opposing jaws fit together when the jaws are closed may lead to the cusps pushing food into food traps.

In some embodiments, tooth mobility may play a role in the creation of food traps. A mobile tooth may be caused by insufficient bone structure around the root or other dental issues. For example, bite forces caused during contact between the teeth of opposing jaws may cause a mobile tooth to move and create a gap and potential food trap between the mobile tooth and an adjacent tooth. Food may be pushed into the gap and become trapped when the jaws separate or open and the mobile tooth moves back to a natural position.

FIG. 2G shows an example of bite contacts that may result in a food trap. For example, tooth 202F may be mobile. In occlusion, tooth 202E may impart forces on tooth 202G and tooth 202F. The forces may cause tooth 202F to move in an anterior direction, opening up and creating a gap in the interproximal space 206 between tooth 202G and tooth 202T. In some embodiments, the tooth cusp 240 of tooth 202E may impart the forces on tooth 202F that cause the tooth 202F to move. Food located caught between 202E of the upper arch and teeth 202G and 202F of the lower arch may be pushed into the gap formed between tooth 202G and 202T while the upper and lower arches are in occlusion. When the arches disocclude, tooth 202F may move back to its normal position and clamp the food pushed into the gap 202G and 202T.

Treatment options to correct bite contacts may include one or more of orthodontic treatment or dental restorations like veneers or bonding to reshape the teeth and correct the bite contacts.

FIG. 2H illustrates how poor gum or gingiva health can lead to food traps in a patient's detention. The tooth 202 has healthy gingiva 210A on a first side and unhealthy gingiva 210B on the second side. The healthy gingiva 210A contacts the tooth from the root all the way up to the crown. The close contact between the gingiva 210A and the tooth 202 aid in supporting the tooth and in preventing food from the enlarged between the healthy gingiva 210A and the tooth 202.

The unhealthy gingiva 210B is separated from the tooth forming a gap 242 between the tooth's crown and root and the gingiva 210B. The gap 242 may become a food trap trapping food between the tooth and the unhealthy gingiva 210B.

The separation of the gingiva from the tooth may be caused by one or more dental problems.

Gum diseases, such as gingivitis and periodontitis, are caused by bacterial infections that can damage gum tissue and the supporting bone structure. As the disease progresses, gums may start to recede, exposing the tooth roots. Brushing teeth too hard or using a toothbrush with hard bristles can cause gum tissue to wear away, leading to gum recession. It is essential to use a soft-bristled toothbrush and apply gentle pressure while brushing. Some people may be genetically predisposed to gum recession due to factors like thin or weak gum tissue or a family history of gum disease.

Teeth that are not properly aligned can cause uneven distribution of forces during biting or chewing, leading to excessive stress on the gum tissue and potentially causing gum recession. Teeth grinding or clenching (bruxism) can impart excessive force on teeth and gum tissue, contributing to gum recession over time. Smoking or using smokeless tobacco products can cause the gum tissue to become irritated and inflamed, increasing the risk of gum recession. Inadequate dental care, including insufficient brushing and flossing, can lead to plaque buildup and tartar formation, resulting in gum disease and subsequent gum recession. Trauma to the teeth or gums, such as from a sports injury or accident, can damage gum tissue and cause recession.

Gum recession in its causes may be treated through improved dental hygiene, corrective orthodontics, or prosthodontics.

FIG. 2I illustrates near-infrared scanning in the detection of food traps in a patient's detention. A dentition model 250 is displayed on the left-hand side of FIG. 2I. The dentition model 250 may be a three-dimensional digital model of the patient's teeth acquired through inter-oral scanning techniques using an intraoral scanner. The three-dimensional model may have color data applied to it in order to represent both the three-dimensional shape and the correct color of the patient's dentition. In some embodiments, as described herein, near-infrared image capture and scanning data may be combined with three-dimensional surface scan data in order to provide additional information to the dental professional or to analysis systems in order to more accurately evaluate the patient's oral health.

The upper right corner shows near-infrared scan data 252. Near-infrared scan data 252 may reveal subsurface structures of the patient's teeth. For example, a subsurface cavity 256 also referred to as a caries may be revealed by the near-infrared data. Caries may begin as subsurface defects in the patient's teeth and may become exposed to the surface. When a caries is on the surface are exposed to the surface of the teeth, the caries may form a food trap. Near-infrared scanning data may reveal the existence of a dental carie before visual external observation would detect the carie.

In some embodiments, the color two-dimensional image 254 may be presented to a dental professional. In some embodiments the two-dimensional color image 254 may be the two-dimensional color image data used to generate the color data on the three-dimensional model 250. In some embodiments the two-dimensional color data may be captured or generated at the same time as the three-dimensional model and the near-infrared color data is captured. In some embodiments it may be captured before or after the three-dimensional data in the near-infrared data is captured.

In some embodiments, other subsurface data may be generated and/or used for detection of food traps. For example, x-ray data may be captured in later aligned with correlated with the three-dimensional model in near-infrared data. In some embodiments cone beam computed tomography (CBCT) scanning may also be used to detect subsurface defects in a patient's dental tissues.

FIG. 2J illustrates cone-beam computed tomography (CBCT) scanning in the detection of food traps in a patient's detention. CBCT scanning is an advanced dental imaging technique that uses a cone shaped X-ray beam to generate three-dimensional (3D) images of a patient's teeth, jaws, and surrounding structures. CBCT scanning provides a more detailed and accurate representation of the patient's anatomy compared to traditional two-dimensional (2D) X-rays, such as periapical or panoramic radiographs.

During a CBCT scan, the X-ray source and detector rotate around the patient's head, capturing multiple images from various angles. These images are then processed to create a single 3D representation of the area of interest or the patient's dental tissues including teeth, jaws, neck and even cars, nose, and throat. CBCT scans expose patients to a lower radiation dose compared to conventional CT scans used in medical imaging, making it a safer option for dental applications.

CBCT scanning offers several advantages in dental evaluation, diagnostics, and treatment planning. CBCT scans help determine the correct position and size of dental implants, assess bone quality and quantity, and identify structures like nerves and blood vessels. CBCT scans can provide a comprehensive view of the teeth and jaw structures, assisting in diagnosing complex orthodontic cases and aid in treatment planning, such as by revealing root positions.

CBCT scans also reveal subsurface defects, included diseases, in dental tissue. For example, the CBCT scan 260 depicts the teeth 202, including the roots 266 embedded within the alveolar bone 262 and the alveolar process 264 that holds the roots in teeth in place. In some embodiments, the CBCT scan may reveal defects in the alveolar bone 262 and the alveolar process 264 that may result in abnormal tooth mobility, such as the tooth mobility issues discussed elsewhere herein.

Returning to FIG. 1, at block 130, data of the location, orientation, and shape of a potential food trap may be generated. The data of the location, orientation, and shape of a potential food trap may be output.

At block 140, the data of the location, orientation, and shape of a potential food trap may be used to provide feedback related to the location, orientation, and shape of a potential food trap. For example, a 2D or 3D image or model of the patient's detention may be displayed on a monitor with the feed back as to the location, orientation, and shape of a potential food trap. Feedback may include highlighting the area or volume on the 2D or 3D image or model of the patient's detention displayed on the monitor. The feedback may also include arrows or other visual indications displayed on the display as to the location, orientation, and shape of a potential food trap.

At block 150, treatment options may be generated and presented for the treatment of the food traps. For example, an orthodontic treatment plan may be generated to move the patient's teeth to cure the food trap or move the teeth in such a way as to put the teeth into an arrangement that they no longer form a food trap. In some embodiments, treatments for gum disease or gum recession may be presented to aid in developing more health gingiva. In some embodiments, prosthodontic treatments, such as veneers, crowns, or other treatments may be generated to remove food traps. Any of the treatments discussed with reference to FIGS. 2A-2J may be generated. At block 150, the treatments may also be carried out. For example, FIGS. 7-10 show systems and methods for orthodontic treatment.

Figure 3:
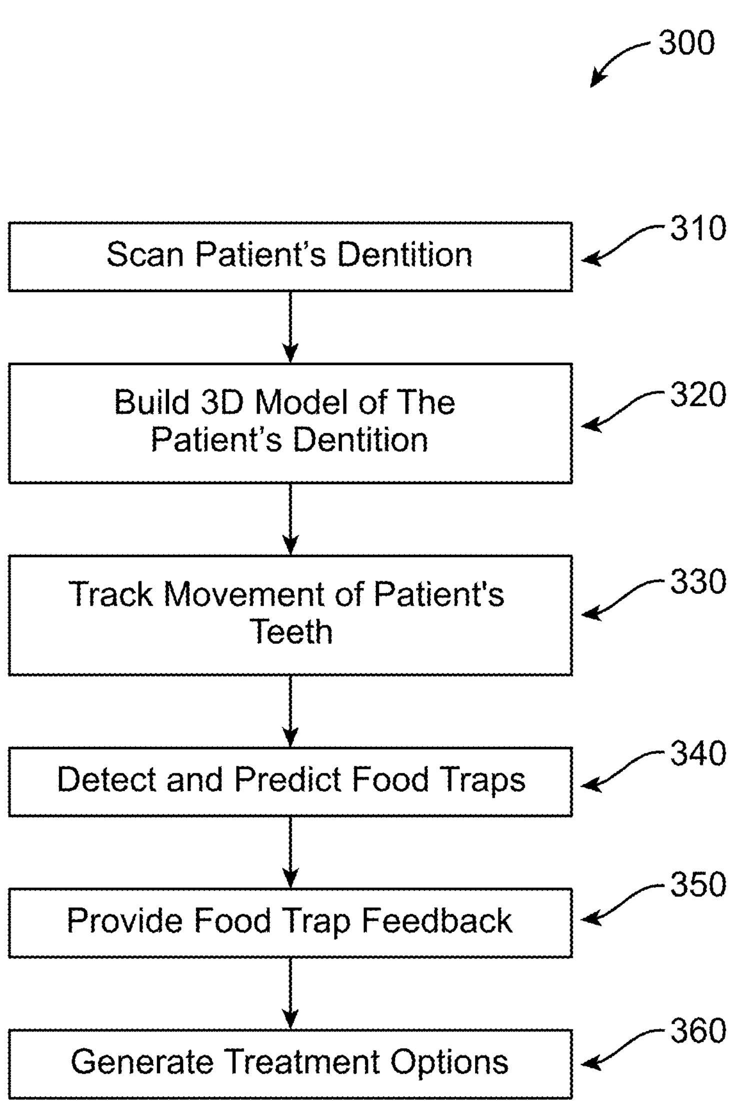
FIG. 3 illustrates an exemplary method of predicting the formation of food traps in a patient's detention, in accordance with embodiments.
Figure 4:
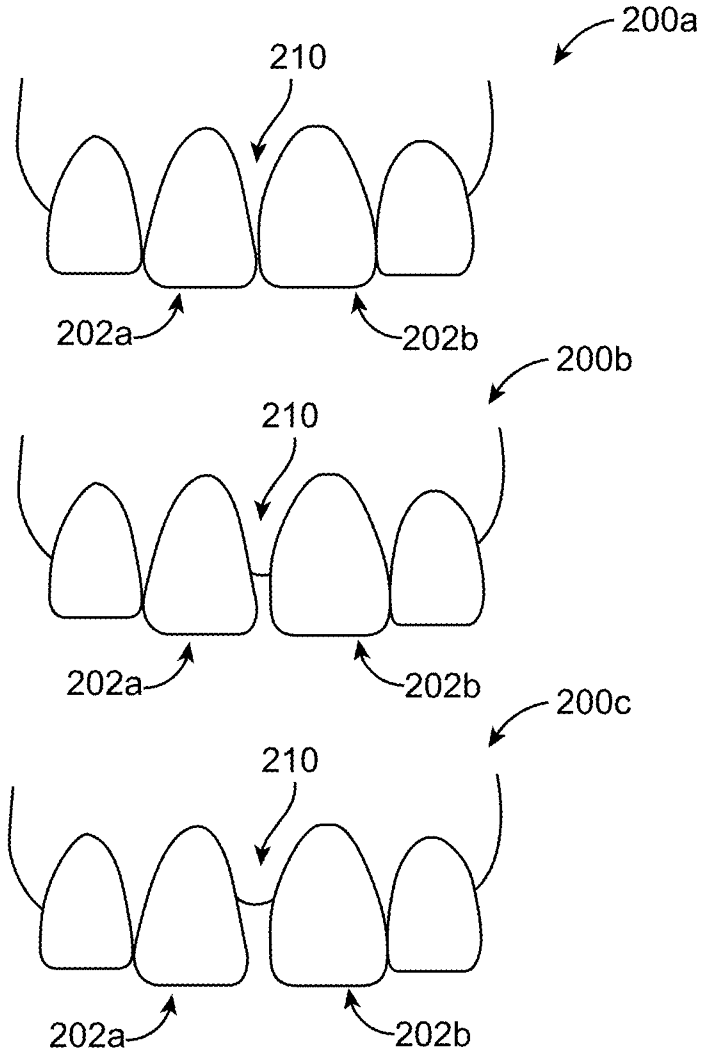
FIG. 4 illustrates an exemplary method of detecting and providing feedback of the existence of food traps in orthodontic treatment and treatment planning, in accordance with embodiments.

FIGS. 3 and 4 illustrate aspects of an exemplary method of predicting the formation of food traps in a patient's detention. The method 300 may include scanning a patient's detention to generate scan data which may include 2D and/or 3D data representing the surface and internal structures of the patient's detention, building a model or models, including a 3D model surface and/or subsurface and volumetric model of the patient's detention based on the scan data, using the scan data and the model(s) to detect the presence of food traps, provide food trap feedback, such as an indication of the location of the possible presence of a food trap or a predicted development of a food trap, and generate treatment options for treating existing food traps or avoid development of food traps, such as through orthodontic treatment.

The method of predicting the formation of food traps 300 may begin at block 310, which includes scanning a patent's dentition at a first point in time, such as an initial dental visit. The patient's dentition may include the tissue and anatomy within the intraoral cavity of the patient, including the patient's teeth, gingiva, jaw bones, and intraoral surfaces of the checks, and lips.

Scanning may include 2D scanning, such as the capture of 2D color images of the surfaces of the patient's dentition, such as the surfaces of the teeth, gingiva, and intraoral surfaces of the checks, and lips. An intraoral scanner may include a color imaging sensor and optics for recording color data during an intraoral scan of the patient. The color data may be corelated with a location in the intraoral cavity to aid in combining the 2D color data with other data captured during an intraoral scan or data of the patient's dentition captured using other systems and methods.

Scanning may also include 3D surface scanning of the patient's dentition, including the intraoral surfaces of the teeth, gingiva, and intraoral surfaces of the checks, and lips. An intraoral scanner may include an imaging sensor and optics for recording 3D data during an intraoral scan of the patient. The 3D data may be point cloud data that is registered together to form a 3D surface model of the patient's dentition. The 3D data may be combined with the 2D color data to create a color 3D surface model of the patient's dentition and/or with other data captured during an intraoral scan or data of the patient's dentition captured using other systems and methods.

Scanning may also include near-infrared scanning of the patient's dentition, including the teeth, gingiva, jaw bones, the checks, and lips. An intraoral scanner may to record near-infrared light and optics for recording near-infrared data during an intraoral scan of the patient.

Near infrared light may penetrate the tissues and anatomy of the patient's intraoral cavity. Near infrared scan data may include data related to the subsurface and internal structures of the patient's anatomy, such as tooth caries, jawbone structure, tooth root position, and shape, gingiva defects, and other internal structures of the patient's anatomy. The near-infrared data may be combined with the 3D data and/or 2D data to add volumetric data to, for example, a 3D surface model of the patient's dentition and/or with other data captured during an intraoral scan or data of the patient's dentition captured using other systems and methods. Combining the 3D surface data with the near-infrared data may include generated a volumetric 3D model of the patient's dentition.

A surface model may include data related to the location, shape, and color of the external surfaces of the patient's dentition. While a 3D surface model may define a volume, it may not have information related to the internal structures within the volume. A volumetric 3D model may include subsurface data and may include information related to the internal structures within a volume defined by the 3D surface data or below the surfaces captured by the 3D scan. An example of near-infrared scan data is provide in FIG. 2I.

Scanning may also include cone-beam computed tomography (CBCT) scanning of the patient's dentition, including the teeth, gingiva, jaw bones, the cheeks, and lips. CBCT scanning is an advanced dental imaging technique that uses a cone shaped X-ray beam to generate three-dimensional (3D) images of a patient's teeth, jaws, and surrounding structures. During a CBCT scan, the X-ray source and detector rotate around the patient's head, capturing multiple images from various angles. These images are then processed to create a single 3D representation of the area of interest or the patient's dental tissues including teeth, jaws, neck and even ears, nose, and throat.

The 3D data generated by a CBCT scan may be combined with the 3D surface data, color data, and/or near-infrared scan data to generate a 3D volumetric model of the patient's detention.

At block 320, a model of the patient's detention may be built. In some embodiments, the model may be built at block 310, such as simultaneously with one or more of the scanning processes described above. The model or models generated through scanning or generated later based on the scan data may be evaluated for the existence of food traps. In some emblements, a single model may be generated that combines aspects of the 3D data, 3D data, near-infrared data, and the CBCT data. In some embodiments, the scan data, including the 3D scan data, the 2D scan data, the Near-infrared scan data, and the CBCT scan data may not be combined in a single model and may instead be separately stored and evaluated for the existence of food traps.

At block 330, the steps carried out in block 310 and 320 may be repeated at a later point in time, such as a follow up visit to a dental professional, to generate second scan data which may include any combination of types of scanning discussed herein. The patient's dentition may be scanned a second time and a second model or models may be built or generated based on the second data. The first model or models generated at blocks 310 and 320 may be compared to the second model or models generated at block 330. Differences in the models may be determined, such as differences in tooth positions and health (including crown and root), gingiva positions and health, and subsurface tissue features and health may be determined. The rate of change may also be determined based on differences in the models, such a rate of tooth movement, a rate of gum recession, a rate of bone or root loss, at etc. The process at block 330 may be treated at additional points in time to generate additional models. The differences between the models at each point in time may be evaluated for the formation of food traps. For example, a growth of the interproximal space between two teeth may indicate a future formation of a food trap.

For example, with reference to FIG. 4, scans of the dentition 200 are shown over time. Dentition 200A is depicts the position of the teeth 202*a*, 2002*b*, and gingiva 210 at a first point in time while dentitions 200*b* and 200*c* show the same patient's detention at later points in time. The separation of the teeth 202*a* and 202*b* from each other and the recession of the gingiva 201 may indicate the formation of a food trap in the interproximal area between the patient's teeth 202*a*, 202*b*. In some embodiments, based on the rate of change in the dentition from the first point in time at dentition 202*a* and the second point in time 202*b*, the method may determine that a food trap may form in the future at that location. By the third point in time, analysis of the dentition 202*c* may indicate the existence of a food trap.

At block 340 the formation of food traps may be predicted or the existence of food traps may be detected based on the scan data. The detection of food traps and a prediction of their future formation may be made based on an evaluation or analysis of the scan data of time, as discussed above. The evaluation or analysis may be carried out in many ways. For example, the position and shape of the patient's teeth may be analyzed based on the 3D surface data. The size and shape of the interproximal region and the angles of the teeth may be extracted from the 3D data to determine if the shape has the qualities of a food trap. Food may be detected in the 3D data or the color data. The existence of food in the patient's detention may indicate the existence of a food trap at that location. A machine learning or artificial intelligence algorithm may be trained based on images and 3D and other scan data tagged with the location of food traps. The trained algorithm may then evaluate the patient's scan data to determine the existence of food traps. FIGS. 2A-2J and the associated text herein, describe the structures and features that may be detected and may indicated the existence of a food trap. At block 340, the structures of the dentition shown and described with respect to FIGS. 2A-2J may be detected.

At block 340, data of the location, orientation, and shape of a potential existing or future food trap may be generated. The data of the location, orientation, and shape of a potential existing or future food trap may be output.

At block 350, the data of the location, orientation, and shape of a potential existing or future food trap may be used to provide feedback related to the location, orientation, and shape of a potential existing or future food trap. For example, a 2D or 3D image or model of the patient's detention may be displayed on a monitor with the feedback as to the location, orientation, and shape of a potential food trap. Feedback may include highlighting the area or volume on the 2D or 3D image or model of the patient's detention displayed on the monitor. The feedback may also include arrows or other visual indications displayed on the display as to the location, orientation, and shape of a potential existing or future food trap.

At block 360, treatment options may be generated and presented for the treatment of the potential existing or future food trap or traps. For example, an orthodontic treatment plan may be generated to move the patient's teeth to cure the food trap or move the teeth in such a way as to put the teeth into an arrangement that they no longer form a food trap. In some embodiments, treatments for gum disease or gum recession may be presented to aid in developing more health gingiva. In some embodiments, prosthodontic treatments, such as veneers, crowns, or other treatments may be generated to remove food traps. Any of the treatments discussed with reference to FIGS. 2A-2J may be generated. At block 360, the treatments may also be carried out. For example, FIGS. 7-10 show systems and methods for orthodontic treatment.

Figure 5:
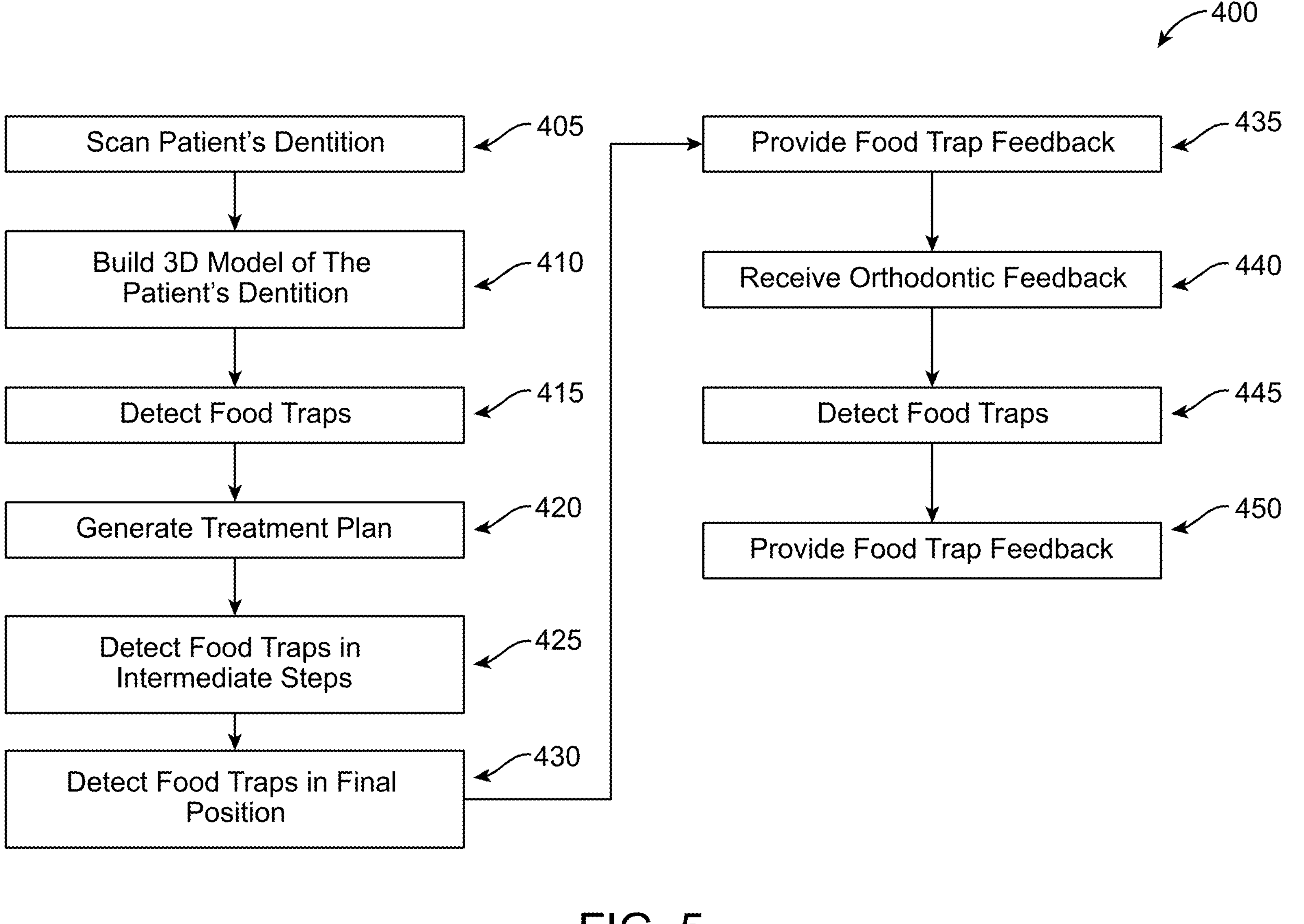
FIG. 5 illustrates an exemplary method of detecting and providing feedback of the existence of food traps in restorative or prosthodontic treatment and treatment planning, in accordance with embodiments.

FIG. 5 illustrates an exemplary method 400 of detecting and providing feedback of the existence of food traps in orthodontic treatment and treatment planning. The method 400 may include scanning a patient's detention to generate scan data which may include 2D and/or 3D data representing the surface and internal structures of the patient's detention, building a model or models, including a 3D model surface and/or subsurface and volumetric model of the patient's detention based on the scan data, using the scan data and the model(s) to detect the presence of food traps, provide food trap feedback, such as an indication of the location of the possible presence of a food trap or a predicted development of a food trap, and generate treatment options for treating existing food traps or avoid development of food traps, such as through modifications to the orthodontic treatment.

The method 400 of detecting and providing feedback of the existence of food traps in orthodontic treatment and treatment planning may begin at block 405, which includes scanning a patent's dentition at a first point in time, such as an initial dental visit. The patient's dentition may include the tissue and anatomy within the intraoral cavity of the patient, including the patient's teeth, gingiva, jaw bones, and intraoral surfaces of the checks, and lips.

Scanning may include 2D scanning, such as the capture of 2D color images of the surfaces of the patient's dentition, such as the surfaces of the teeth, gingiva, and intraoral surfaces of the checks, and lips. An intraoral scanner may include a color imaging sensor and optics for recording color data during an intraoral scan of the patient. The color data may be corelated with a location in the intraoral cavity to aid in combining the 2D color data with other data captured during an intraoral scan or data of the patient's dentition captured using other systems and methods.

Scanning may also include 3D surface scanning of the patient's dentition, including the intraoral surfaces of the teeth, gingiva, and intraoral surfaces of the cheeks, and lips. An intraoral scanner may include an imaging sensor and optics for recording 3D data during an intraoral scan of the patient. The 3D data may be point cloud data that is registered together to form a 3D surface model of the patient's dentition. The 3D data may be combined with the 2D color data to create a color 3D surface model of the patient's dentition and/or with other data captured during an intraoral scan or data of the patient's dentition captured using other systems and methods.

Scanning may also include near-infrared scanning of the patient's dentition, including the teeth, gingiva, jaw bones, the cheeks, and lips. An intraoral scanner may to record near-infrared light and optics for recording near-infrared data during an intraoral scan of the patient.

Near infrared light may penetrate the tissues and anatomy of the patient's intraoral cavity. Near infrared scan data may include data related to the subsurface and internal structures of the patient's anatomy, such as tooth caries, jawbone structure, tooth root position, and shape, gingiva defects, and other internal structures of the patient's anatomy. The near-infrared data may be combined with the 3D data and/or 2D data to add volumetric data to, for example, a 3D surface model of the patient's dentition and/or with other data captured during an intraoral scan or data of the patient's dentition captured using other systems and methods. Combining the 3D surface data with the near-infrared data may include generated a volumetric 3D model of the patient's dentition.

A surface model may include data related to the location, shape, and color of the external surfaces of the patient's dentition. While a 3D surface model may define a volume, it may not have information related to the internal structures within the volume. A volumetric 3D model may include subsurface data and may include information related to the internal structures within a volume defined by the 3D surface data or below the surfaces captured by the 3D scan. An example of near-infrared scan data is provide in FIG. 2I.

Scanning may also include cone-beam computed tomography (CBCT) scanning of the patient's dentition, including the teeth, gingiva, jaw bones, the cheeks, and lips. CBCT scanning is an advanced dental imaging technique that uses a cone shaped X-ray beam to generate three-dimensional (3D) images of a patient's teeth, jaws, and surrounding structures. During a CBCT scan, the X-ray source and detector rotate around the patient's head, capturing multiple images from various angles. These images are then processed to create a single 3D representation of the area of interest or the patient's dental tissues including teeth, jaws, neck and even ears, nose, and throat.

The 3D data generated by a CBCT scan may be combined with the 3D surface data, color data, and/or near-infrared scan data to generate a 3D volumetric model of the patient's detention.

At block 410, a model of the patient's detention may be built. In some embodiments, the model may be built at block 405, such as simultaneously with one or more of the scanning processes described above. The model or models generated through scanning or generated later based on the scan data may be evaluated for the existence of food traps. In some emblements, a single model may be generated that combines aspects of the 3D data, 3D data, near-infrared data, and the CBCT data. In some embodiments, the scan data, including the 3D scan data, the 2D scan data, the Near-infrared scan data, and the CBCT scan data may not be combined in a single model and may instead be separately stored and evaluated for the existence of food traps.

At block 415 the formation of food traps may be predicted or the existence of food traps may be detected based on the scan data. The detection of food traps and a prediction of their future formation may be made based on an evaluation or analysis of the scan data of time, as discussed above. The evaluation or analysis may be carried out in many ways. For example, the position and shape of the patient's teeth may be analyzed based on the 3D surface data. The size and shape of the interproximal region and the angles of the teeth may be extracted from the 3D data to determine if the shape has the qualities of a food trap. Food may be detected in the 3D data or the color data. The existence of food in the patient's detention may indicate the existence of a food trap at that location. A machine learning or artificial intelligence algorithm may be trained based on images and 3D and other scan data tagged with the location of food traps. The trained algorithm may then evaluate the patient's scan data to determine the existence of food traps. FIGS. 2A-2J and the associated text herein, describe the structures and features that may be detected and may indicated the existence of a food trap. At block 415, the structures of the dentition shown and described with respect to FIGS. 2A-2J may be detected.

At block 415, data of the location, orientation, and shape of a potential existing or future food trap may be generated. The data of the location, orientation, and shape of a potential existing or future food trap may be output.

At block 415, the data of the location, orientation, and shape of a potential existing or future food trap may be used to provide feedback related to the location, orientation, and shape of a potential existing or future food trap. For example, a 2D or 3D image or model of the patient's detention may be displayed on a monitor with the feedback as to the location, orientation, and shape of a potential food trap. Feedback may include highlighting the area or volume on the 2D or 3D image or model of the patient's detention displayed on the monitor. The feedback may also include arrows or other visual indications displayed on the display as to the location, orientation, and shape of a potential existing or future food trap.

At block 415, treatment options may be generated and presented for the treatment of the potential existing or future food trap or traps. For example, an orthodontic treatment plan may be generated to move the patient's teeth to cure the food trap or move the teeth in such a way as to put the teeth into an arrangement that they no longer form a food trap. In some embodiments, treatments for gum disease or gum recession may be presented to aid in developing more health gingiva. In some embodiments, prosthodontic treatments, such as veneers, crowns, or other treatments may be generated to remove food traps. Any of the treatments discussed with reference to FIGS. 2A-2J may be generated. For example, FIGS. 7-10 show systems and methods for orthodontic treatment.

At block 420 an orthodontic treatment plan may be generated. An orthodontic treatment plan may include an initial arrangement of the patient's teeth, a final arrangement of a patient's teeth, and one or more intermediate stages to move the patient's teeth from the initial arrangements towards the final arrangements, as described in more detail with respect to FIGS. 7-10.

At block 425, each of the intermediate stages of the treatment plan may be evaluated to detect possible food traps. At block 425 the formation of food traps may be predicted or the existence of food traps may be detected based on the scan data. The detection of food traps and a prediction of their future formation may be made based on an evaluation or analysis of the scan data of time, as discussed above. The evaluation or analysis may be carried out in many ways. For example, the position and shape of the patient's teeth may be analyzed based on the 3D surface data. The size and shape of the interproximal region and the angles of the teeth may be extracted from the 3D data to determine if the shape has the qualities of a food trap. Food may be detected in the 3D data or the color data. The existence of food in the patient's detention may indicate the existence of a food trap at that location. A machine learning or artificial intelligence algorithm may be trained based on images and 3D and other scan data tagged with the location of food traps. The trained algorithm may then evaluate the patient's scan data to determine the existence of food traps. FIGS. 2A-2J and the associated text herein, describe the structures and features that may be detected and may indicated the existence of a food trap. At block 425, the structures of the dentition shown and described with respect to FIGS. 2A-2J may be detected.

At block 425, data of the location, orientation, and shape of a potential existing or future food trap may be generated. The data of the location, orientation, and shape of a potential existing or future food trap may be output.

At block 430, the final position of the teeth in the treatment plan may be evaluated to detect possible food traps. At block 430 the formation of food traps may be predicted or the existence of food traps may be detected based on the scan data. The detection of food traps and a prediction of their future formation may be made based on an evaluation or analysis of the scan data of time, as discussed above. The evaluation or analysis may be carried out in many ways. For example, the position and shape of the patient's teeth may be analyzed based on the 3D surface data. The size and shape of the interproximal region and the angles of the teeth may be extracted from the 3D data to determine if the shape has the qualities of a food trap. Food may be detected in the 3D data or the color data. The existence of food in the patient's detention may indicate the existence of a food trap at that location. A machine learning or artificial intelligence algorithm may be trained based on images and 3D and other scan data tagged with the location of food traps. The trained algorithm may then evaluate the patient's scan data to determine the existence of food traps. FIGS. 2A-2J and the associated text herein, describe the structures and features that may be detected and may indicated the existence of a food trap. At block 430, the structures of the dentition shown and described with respect to FIGS. 2A-2J may be detected.

At block 430, data of the location, orientation, and shape of a potential existing or future food trap may be generated. The data of the location, orientation, and shape of a potential existing or future food trap may be output.

At block 435, the data of the location, orientation, and shape of a potential food trap or traps in the intermediate or final positions may be used to provide feedback related to the location, orientation, and shape of any potential food traps. For example, a 2D or 3D image or model of the patient's detention in the intermediate or final stages may be displayed on a monitor with the feed back as to the location, orientation, and shape of a potential food trap. Feedback may include highlighting the area or volume on the 2D or 3D image or model of the patient's detention displayed on the monitor. The feedback may also include arrows or other visual indications displayed on the display as to the location, orientation, and shape of a potential food trap.

At block 440, orthodontic feedback may be received. The orthodontic feedback may include repositioning of the patient's teeth in any of the intermediate or final positions. After receiving the feedback, at block 445, the final and intermediate positions of the patient's teeth may be evaluated to detect for potential food traps, as described herein, such as with resect to blocks 425 and 430.

Additional food trap feedback based on the orthodontic feedback may be provided, as described herein, such as with respect to block 435.

Figure 6:
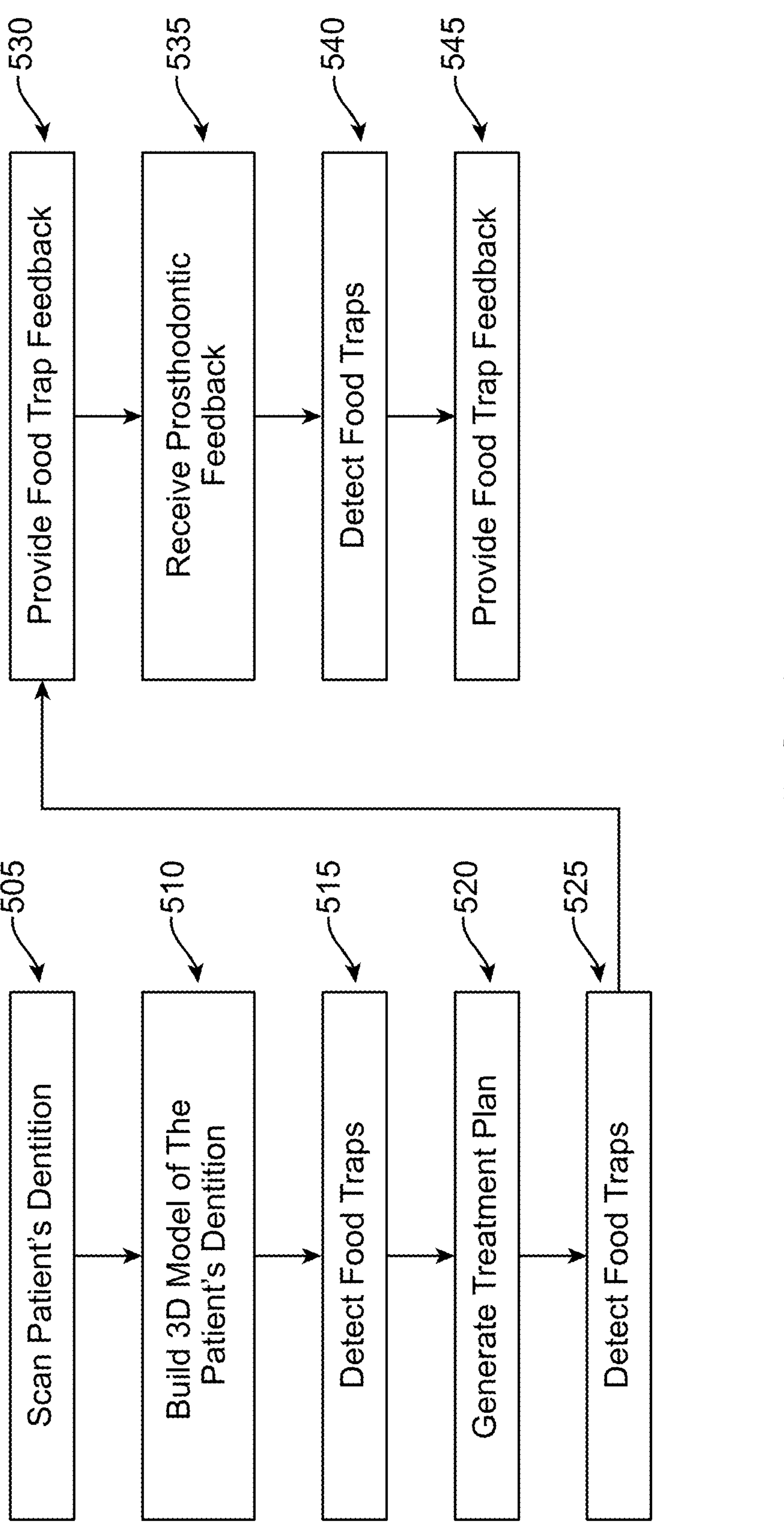
FIG. 6 illustrates an exemplary tooth repositioning appliance or aligner that can be worn by a patient in order to achieve an incremental repositioning of individual teeth in the jaw, in accordance with some embodiments.

FIG. 6 illustrates an exemplary method of detecting and providing feedback of the existence of food traps in restorative or prosthodontic treatment and treatment planning. The method 500 may include scanning a patient's detention to generate scan data which may include 2D and/or 3D data representing the surface and internal structures of the patient's detention, building a model or models, including a 3D model surface and/or subsurface and volumetric model of the patient's detention based on the scan data, using the scan data and the model(s) to detect the presence of food traps, provide food trap feedback, such as an indication of the location of the possible presence of a food trap or a predicted development of a food trap, and generate treatment options for treating existing food traps or avoid development of food traps, such as through modifications to the prosthodontic treatment.

The method 500 of detecting and providing feedback of the existence of food traps in prosthodontic treatment and treatment planning may begin at block 505, which includes scanning a patent's dentition at a first point in time, such as an initial dental visit. The patient's dentition may include the tissue and anatomy within the intraoral cavity of the patient, including the patient's teeth, gingiva, jaw bones, and intraoral surfaces of the checks, and lips.

Scanning may include 2D scanning, such as the capture of 2D color images of the surfaces of the patient's dentition, such as the surfaces of the teeth, gingiva, and intraoral surfaces of the cheeks, and lips. An intraoral scanner may include a color imaging sensor and optics for recording color data during an intraoral scan of the patient. The color data may be corelated with a location in the intraoral cavity to aid in combining the 2D color data with other data captured during an intraoral scan or data of the patient's dentition captured using other systems and methods.

Scanning may also include 3D surface scanning of the patient's dentition, including the intraoral surfaces of the teeth, gingiva, and intraoral surfaces of the checks, and lips. An intraoral scanner may include an imaging sensor and optics for recording 3D data during an intraoral scan of the patient. The 3D data may be point cloud data that is registered together to form a 3D surface model of the patient's dentition. The 3D data may be combined with the 2D color data to create a color 3D surface model of the patient's dentition and/or with other data captured during an intraoral scan or data of the patient's dentition captured using other systems and methods.

Scanning may also include near-infrared scanning of the patient's dentition, including the teeth, gingiva, jaw bones, the checks, and lips. An intraoral scanner may include a near-infrared light source and imaging sensor that is sensitive to and configured to record near-infrared light and optics for recording near-infrared data during an intraoral scan of the patient.

Near infrared light may penetrate the tissues and anatomy of the patient's intraoral cavity. Near infrared scan data may include data related to the subsurface and internal structures of the patient's anatomy, such as tooth caries, jawbone structure, tooth root position, and shape, gingiva defects, and other internal structures of the patient's anatomy. The near-infrared data may be combined with the 3D data and/or 2D data to add volumetric data to, for example, a 3D surface model of the patient's dentition and/or with other data captured during an intraoral scan or data of the patient's dentition captured using other systems and methods. Combining the 3D surface data with the near-infrared data may include generated a volumetric 3D model of the patient's dentition.

A surface model may include data related to the location, shape, and color of the external surfaces of the patient's dentition. While a 3D surface model may define a volume, it may not have information related to the internal structures within the volume. A volumetric 3D model may include subsurface data and may include information related to the internal structures within a volume defined by the 3D surface data or below the surfaces captured by the 3D scan. An example of near-infrared scan data is provide in FIG. 2I.

Scanning may also include cone-beam computed tomography (CBCT) scanning of the patient's dentition, including the teeth, gingiva, jaw bones, the cheeks, and lips. CBCT scanning is an advanced dental imaging technique that uses a cone shaped X-ray beam to generate three-dimensional (3D) images of a patient's teeth, jaws, and surrounding structures. During a CBCT scan, the X-ray source and detector rotate around the patient's head, capturing multiple images from various angles. These images are then processed to create a single 3D representation of the area of interest or the patient's dental tissues including teeth, jaws, neck and even ears, nose, and throat.

The 3D data generated by a CBCT scan may be combined with the 3D surface data, color data, and/or near-infrared scan data to generate a 3D volumetric model of the patient's detention.

At block 510, a model of the patient's detention may be built. In some embodiments, the model may be built at block 505, such as simultaneously with one or more of the scanning processes described above. The model or models generated through scanning or generated later based on the scan data may be evaluated for the existence of food traps. In some emblements, a single model may be generated that combines aspects of the 3D data, 3D data, near-infrared data, and the CBCT data. In some embodiments, the scan data, including the 3D scan data, the 2D scan data, the Near-infrared scan data, and the CBCT scan data may not be combined in a single model and may instead be separately stored and evaluated for the existence of food traps.

At block 515 the formation of food traps may be predicted or the existence of food traps may be detected based on the scan data. The detection of food traps and a prediction of their future formation may be made based on an evaluation or analysis of the scan data of time, as discussed above. The evaluation or analysis may be carried out in many ways. For example, the position and shape of the patient's teeth may be analyzed based on the 3D surface data. The size and shape of the interproximal region and the angles of the teeth may be extracted from the 3D data to determine if the shape has the qualities of a food trap. Food may be detected in the 3D data or the color data. The existence of food in the patient's detention may indicate the existence of a food trap at that location. A machine learning or artificial intelligence algorithm may be trained based on images and 3D and other scan data tagged with the location of food traps. The trained algorithm may then evaluate the patient's scan data to determine the existence of food traps. FIGS. 2A-2J and the associated text herein, describe the structures and features that may be detected and may indicated the existence of a food trap. At block 515, the structures of the dentition shown and described with respect to FIGS. 2A-2J may be detected.

At block 515, data of the location, orientation, and shape of a potential existing or future food trap may be generated. The data of the location, orientation, and shape of a potential existing or future food trap may be output.

At block 515, the data of the location, orientation, and shape of a potential existing or future food trap may be used to provide feedback related to the location, orientation, and shape of a potential existing or future food trap. For example, a 2D or 3D image or model of the patient's detention may be displayed on a monitor with the feedback as to the location, orientation, and shape of a potential food trap. Feedback may include highlighting the area or volume on the 2D or 3D image or model of the patient's detention displayed on the monitor. The feedback may also include arrows or other visual indications displayed on the display as to the location, orientation, and shape of a potential existing or future food trap.

At block 515, treatment options may be generated and presented for the treatment of the potential existing or future food trap or traps. For example, a prosthodontic treatment plan may be generated to cure the food trap or move the teeth in such a way as to put the teeth into an arrangement that they no longer form a food trap. In some embodiments, treatments for gum disease or gum recession may be presented to aid in developing more health gingiva. In some embodiments, prosthodontic treatments, such as veneers, crowns, or other treatments may be generated to remove food traps. Any of the treatments discussed with reference to FIGS. 2A-2J may be generated. At block 360, the treatments may also be carried out.

At block 520 a prosthodontic treatment plan may be generated. A prosthodontic treatment plan may include a shape and position of one or more of the patient's teeth and a corresponding one or more prosthetics, such as a crown, bridge, dentures, etc.

At block 525, each of the prosthodontic treatment plan may be evaluated to detect possible food traps. At block 525 the formation of food traps may be predicted or the existence of food traps may be detected based on the scan data. The detection of food traps and a prediction of their future formation may be made based on an evaluation or analysis of the scan data of time, as discussed above. The evaluation or analysis may be carried out in many ways. For example, the position and shape of the patient's teeth and prosthodontics may be analyzed based on the 3D surface data and the models of the treatment plan. The size and shape of a margin line and how a crown interfaces with a prepared tooth may be extracted from the 3D data to determine if the shape has the qualities of a food trap. A machine learning or artificial intelligence algorithm may be trained based on images and 3D and other scan data tagged with the location of food traps. The trained algorithm may then evaluate the patient's scan data to determine the existence of food traps. FIGS. 2A-2J and the associated text herein, describe the structures and features that may be detected and may indicated the existence of a food trap. At block 525, the structures of the dentition shown and described with respect to FIGS. 2A-2J may be detected.

At block 525, data of the location, orientation, and shape of a potential existing or future food trap may be generated. The data of the location, orientation, and shape of a potential existing or future food trap may be output.

At block 530, the data of the location, orientation, and shape of a potential food trap or traps in the intermediate or final positions may be used to provide feedback related to the location, orientation, and shape of any potential food traps. For example, a 2D or 3D image or model of the patient's detention in the intermediate or final stages may be displayed on a monitor with the feedback as to the location, orientation, and shape of a potential food trap. Feedback may include highlighting the area or volume on the 2D or 3D image or model of the patient's detention displayed on the monitor. The feedback may also include arrows or other visual indications displayed on the display as to the location, orientation, and shape of a potential food trap.

At block 535, prosthodontic feedback may be received. The prosthodontic feedback may include repositioning or reshaping of the patient's teeth or changes to the shape and/or position of a dental prosthetic in any of the intermediate or final positions. After receiving the feedback, at block 540, the final and intermediate positions of the patient's teeth may be evaluated to detect for potential food traps, as described herein, such as with respect to 525.

Additional food trap feedback based on the prosthodontic feedback may be provided, as described herein, such as with respect to block 545.

Figure 7:
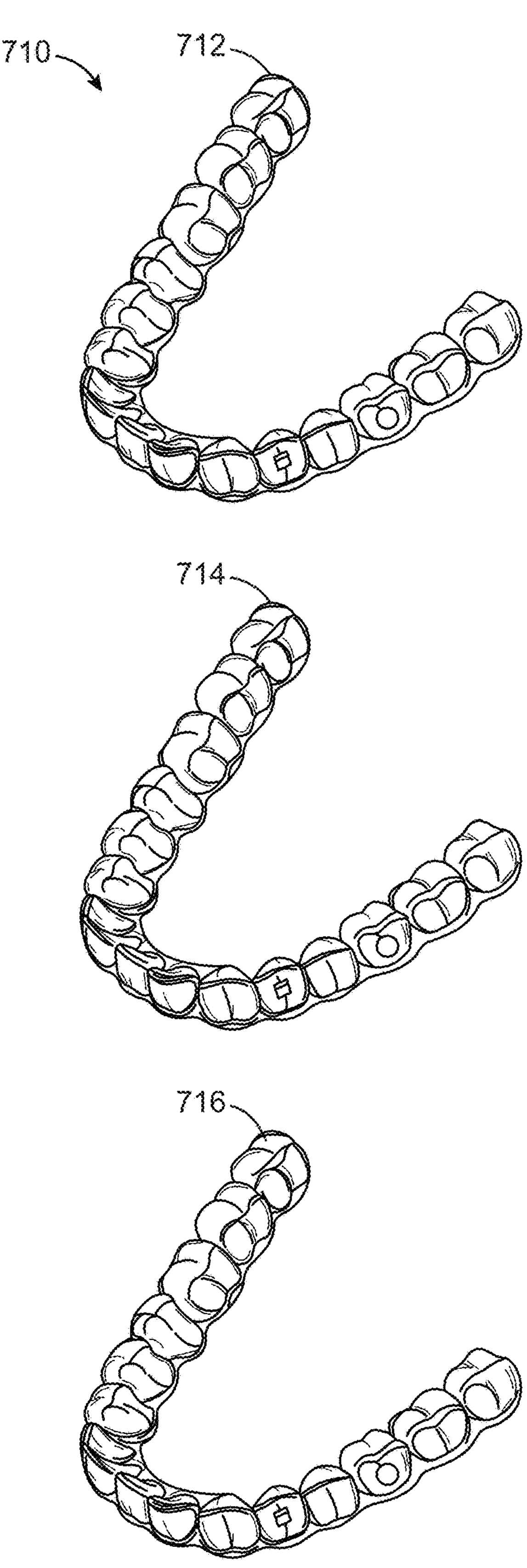
FIG. 7 illustrates a tooth repositioning system, in accordance with some embodiments.

FIG. 7 illustrates an exemplary tooth repositioning appliance 700, such as an aligner that can be worn by a patient in order to achieve an incremental repositioning of individual teeth 702 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient. In some embodiments, no wires or other means will be provided for holding an appliance in place over the teeth. In some cases, however, it may be desirable or necessary to provide individual attachments or other anchoring elements 704 on teeth 702 with corresponding receptacles or apertures 706 in the appliance 700 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830, 450.

FIG. 7 illustrates a tooth repositioning system 701 including a plurality of appliances 703A, 703B, 703C. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 701 can include a first appliance 703A corresponding to an initial tooth arrangement, one or more intermediate appliances 703B corresponding to one or more intermediate arrangements, and a final appliance 703C corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 8:
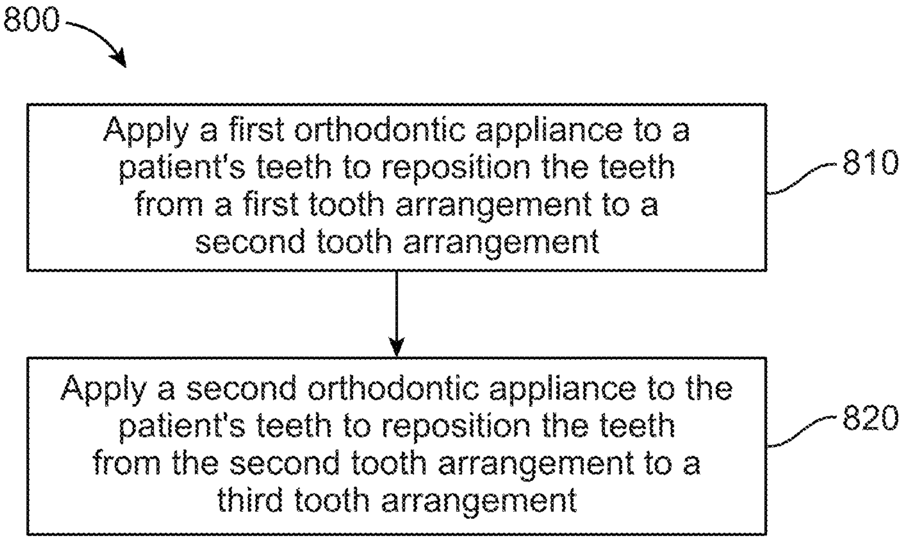
FIG. 8 shows a method of orthodontic treatment using a plurality of appliances, in accordance with embodiments.

FIG. 8 illustrates a method 800 of orthodontic treatment using a plurality of appliances, in accordance with many embodiments. The method 800 can be practiced using any of the appliances or appliance sets described herein. In step 810, a first orthodontic appliance is applied to a patient's teeth in order to reposition the teeth from a first tooth arrangement to a second tooth arrangement. In step 820, a second orthodontic appliance is applied to the patient's teeth in order to reposition the teeth from the second tooth arrangement to a third tooth arrangement. The method 800 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 9:
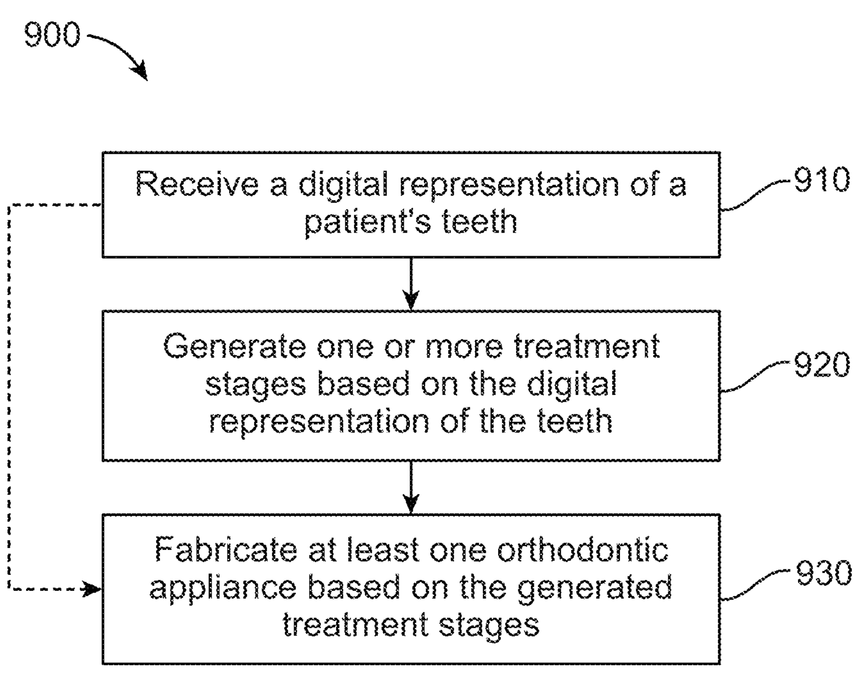
FIG. 9 shows a method for digitally planning an orthodontic treatment, in accordance with embodiments.

FIG. 9 illustrates a method 900 for digitally planning an orthodontic treatment and/or design or fabrication of an appliance, in accordance with many embodiments. The method 900 can be applied to any of the treatment procedures described herein and can be performed by any suitable data processing system. Any embodiment of the appliances described herein can be designed or fabricated using the method 900.

In step 910, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 920, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 930, at least one orthodontic appliance is fabricated based on the generated treatment stages. For example, a set of appliances can be fabricated to be sequentially worn by the patient to incrementally reposition the teeth from the initial arrangement to the target arrangement. Some of the appliances can be shaped to accommodate a tooth arrangement specified by one of the treatment stages. Alternatively or in combination, some of the appliances can be shaped to accommodate a tooth arrangement that is different from the target arrangement for the corresponding treatment stage. For example, as previously described herein, an appliance may have a geometry corresponding to an overcorrected tooth arrangement. Such an appliance may be used to ensure that a suitable amount of force is expressed on the teeth as they approach or attain their desired target positions for the treatment stage. As another example, an appliance can be designed in order to apply a specified force system on the teeth and may not have a geometry corresponding to any current or planned arrangement of the patient's teeth.

In some instances, staging of various arrangements or treatment stages may not be necessary for design and/or fabrication of an appliance. As illustrated by the dashed line in FIG. 9, design and/or fabrication of an orthodontic appliance, and perhaps a particular orthodontic treatment, may include use of a representation of the patient's teeth (e.g., receive a digital representation of the patient's teeth 410), followed by design and/or fabrication of an orthodontic appliance based on a representation of the patient's teeth in the arrangement represented by the received representation.

Figure 10:
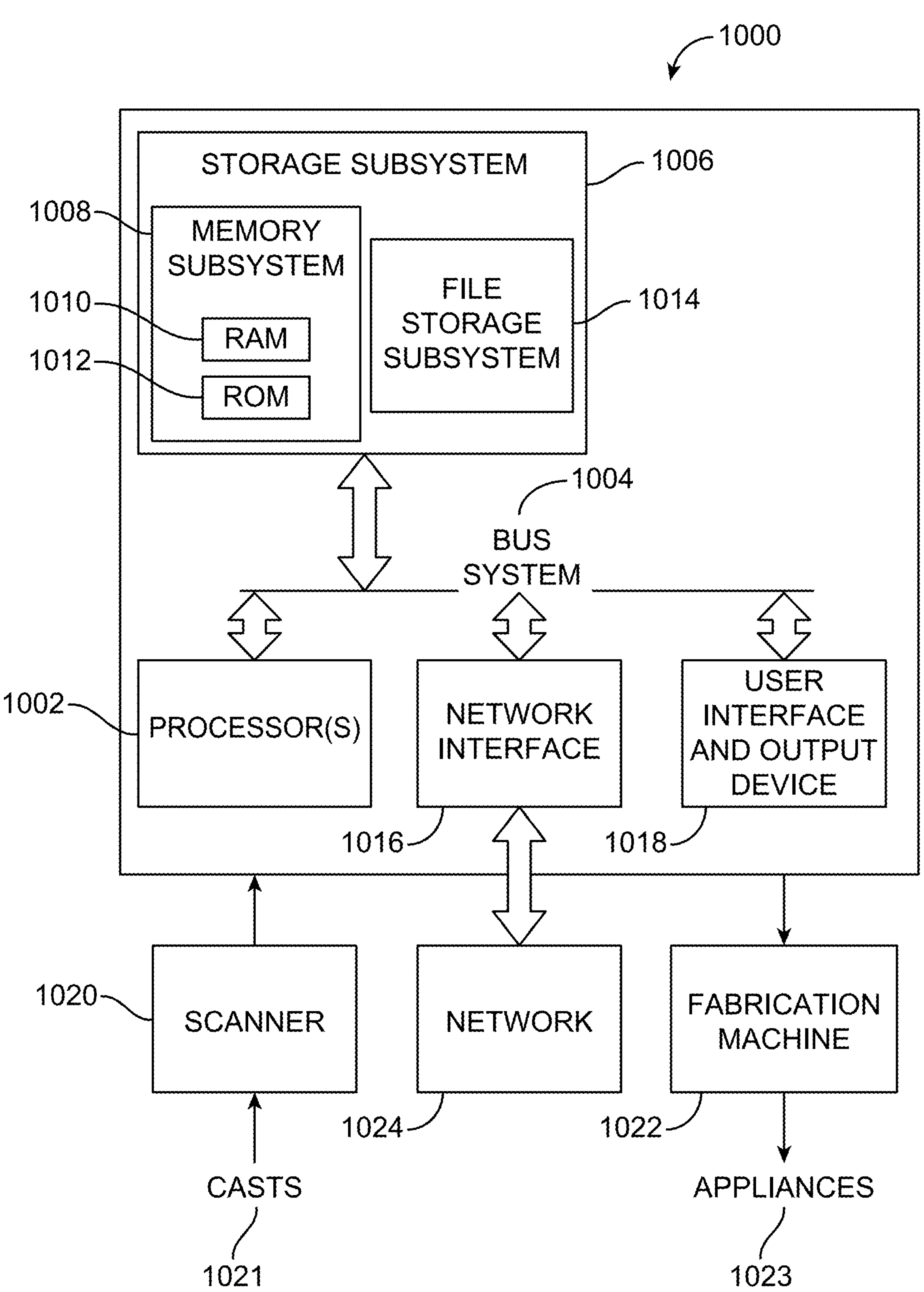
FIG. 10 shows a simplified block diagram of a data processing system, in accordance with embodiments.
Figure 11:
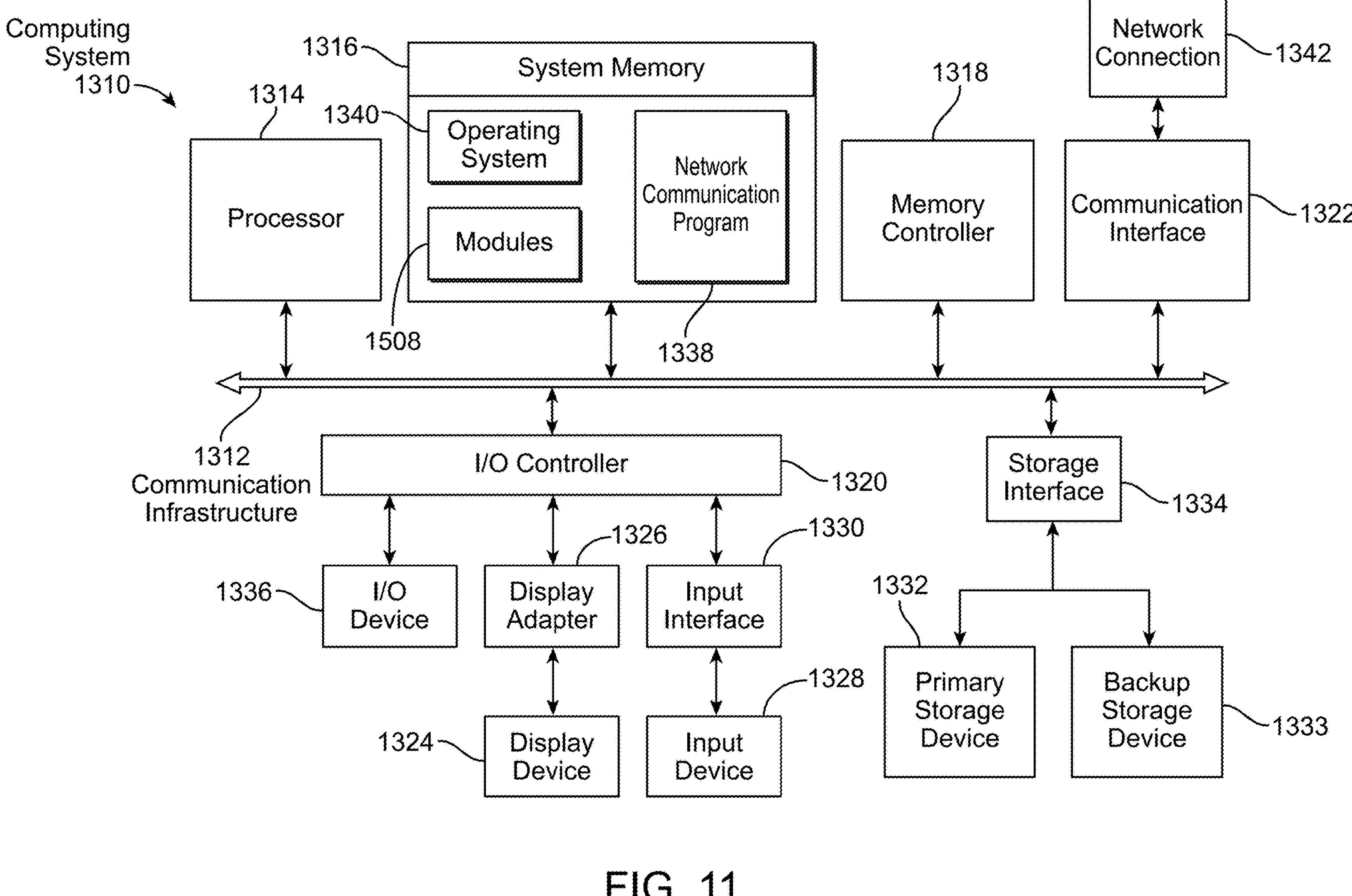
FIG. 11 shows a block diagram of an example computing system capable of implementing one or more embodiments described and/or illustrated herein, in accordance with embodiments.

FIG. 10 is a simplified block diagram of a data processing system 1000 that may be used in executing methods and processes described herein. The data processing system 1000 typically includes at least one processor 1002 that communicates with one or more peripheral devices via bus subsystem 1004. These peripheral devices typically include a storage subsystem 1006 (memory subsystem 1008 and file storage subsystem 1014), a set of user interface input and output devices 1018, and an interface to outside networks 1016. This interface is shown schematically as "Network Interface" block 1016, and is coupled to corresponding interface devices in other data processing systems via communication network interface 1024. Data processing system 1000 can include, for example, one or more computers, such as a personal computer, workstation, mainframe, laptop, and the like.

The user interface input devices 1018 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 1006 maintains the basic required programming, including computer readable media having instructions (e.g., operating instructions, etc.), and data constructs. The program modules discussed herein are typically stored in storage subsystem 1006. Storage subsystem 1006 typically includes memory subsystem 508 and file storage subsystem 1014. Memory subsystem 1008 typically includes a number of memories (e.g., RAM 1010, ROM 1012, etc.) including computer readable memory for storage of fixed instructions, instructions and data during program execution, basic input/output system, etc. File storage subsystem 1014 provides persistent (non-volatile) storage for program and data files, and can include one or more removable or fixed drives or media, hard disk, floppy disk, CD-ROM, DVD, optical drives, and the like. One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 1020 includes any means for obtaining a digital representation (e.g., images, surface topography data, etc.) of a patient's teeth (e.g., by scanning physical models of the teeth such as casts 1021, by scanning impressions taken of the teeth, or by directly scanning the intraoral cavity), which can be obtained either from the patient or from treating professional, such as an orthodontist, and includes means of providing the digital representation to data processing system 1000 for further processing. Scanner 1020 may be located at a location remote with respect to other components of the system and can communicate image data and/or information to data processing system 1000, for example, via a network interface 1024. Fabrication system 1022 fabricates appliances 1023 based on a treatment plan, including data set information received from data processing system 1000. Fabrication machine 1022 can, for example, be located at a remote location and receive data set information from data processing system 1000 via network interface 1024.

Computing System

Figure 12:
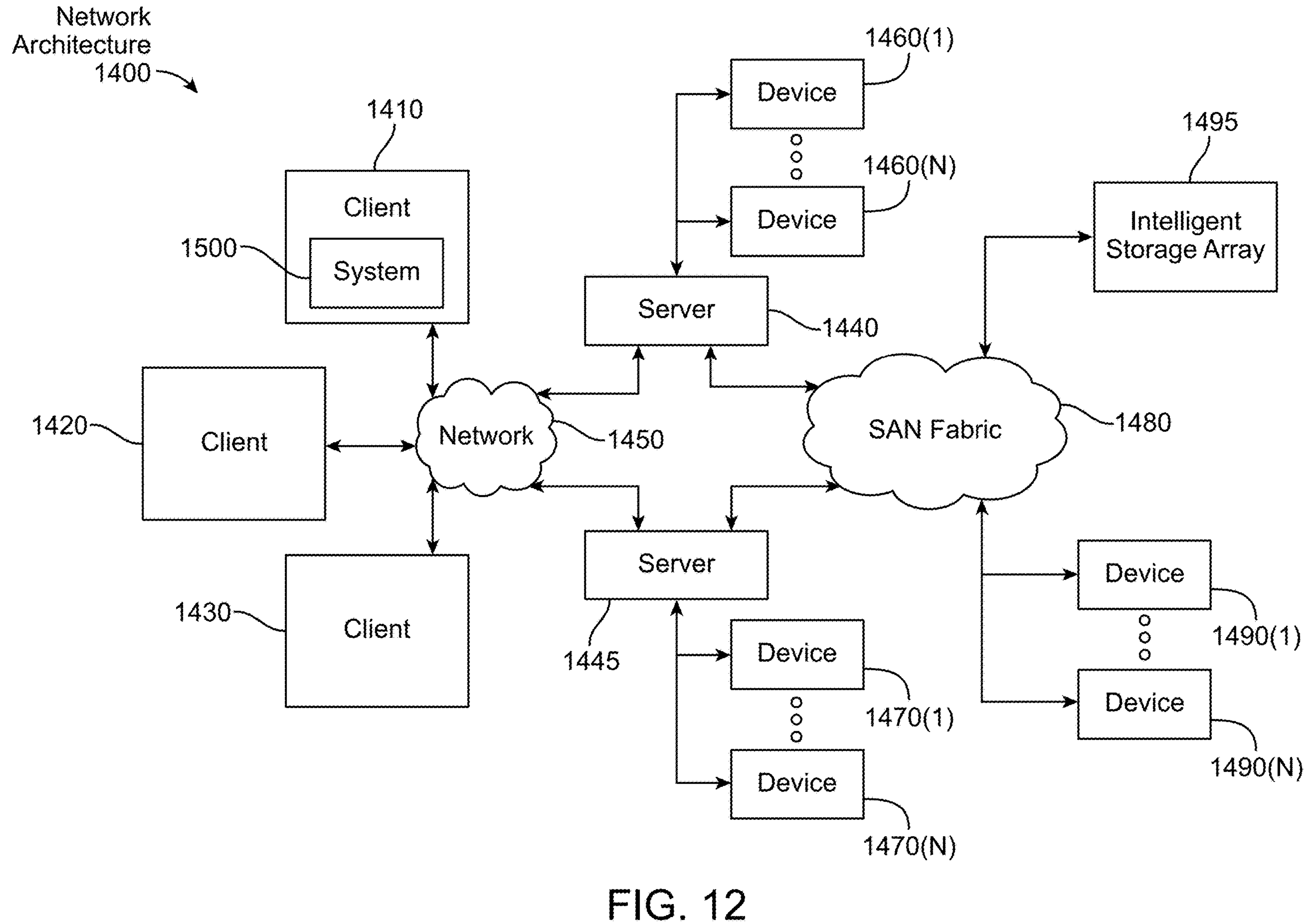
FIG. 12 shows a block diagram of an example computing network capable of implementing one or more of the embodiments described and/or illustrated herein, in accordance with embodiments.

FIG. 12 is a block diagram of an example computing system 1310 capable of implementing one or more of the embodiments described and/or illustrated herein. For example, all or a portion of computing system 1310 may perform and/or be a means for performing, cither alone or in combination with other elements, one or more of the steps described herein (such as one or more of the steps illustrated in FIGS. 1-10. All or a portion of computing system 1310 may also perform and/or be a means for performing any other steps, methods, or processes described and/or illustrated herein.

Computing system 1310 broadly represents any single or multi-processor computing device or system capable of executing computer-readable instructions. Examples of computing system 1310 include, without limitation, workstations, laptops, client-side terminals, servers, distributed computing systems, handheld devices, or any other computing system or device. In its most basic configuration, computing system 1310 may include at least one processor 1314 and a system memory 1316.

Processor 1314 generally represents any type or form of physical processing unit (e.g., a hardware-implemented central processing unit) capable of processing data or interpreting and executing instructions. In certain embodiments, processor 1314 may receive instructions from a software application or module. These instructions may cause processor 1314 to perform the functions of one or more of the example embodiments described and/or illustrated herein.

System memory 1316 generally represents any type or form of volatile or non-volatile storage device or medium capable of storing data and/or other computer-readable instructions. Examples of system memory 1316 include, without limitation, Random Access Memory (RAM), Read Only Memory (ROM), flash memory, or any other suitable memory device. Although not required, in certain embodiments computing system 1310 may include both a volatile memory unit (such as, for example, system memory 1316) and a non-volatile storage device (such as, for example, primary storage device 1332, as described in detail below).

In some examples, system memory 1316 may store and/or load an operating system 1340 for execution by processor 1314. In one example, operating system 1340 may include and/or represent software that manages computer hardware and software resources and/or provides common services to computer programs and/or applications on computing system 1310. Examples of operating system 1340 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 1310 may also include one or more components or elements in addition to processor 1314 and system memory 1316. For example, as illustrated in FIG. 12, computing system 1310 may include a memory controller 1318, an Input/Output (I/O) controller 1320, and a communication interface 1322, each of which may be interconnected via a communication infrastructure 1312. Communication infrastructure 1312 generally represents any type or form of infrastructure capable of facilitating communication between one or more components of a computing device. Examples of communication infrastructure 1312 include, without limitation, a communication bus (such as an Industry Standard Architecture (ISA), Peripheral Component Interconnect (PCI), PCI Express (PCIe), or similar bus) and a network.

Memory controller 1318 generally represents any type or form of device capable of handling memory or data or controlling communication between one or more components of computing system 1310. For example, in certain embodiments memory controller 1318 may control communication between processor 1314, system memory 1316, and I/O controller 1320 via communication infrastructure 1312.

I/O controller 1320 generally represents any type or form of module capable of coordinating and/or controlling the input and output functions of a computing device. For example, in certain embodiments I/O controller 1320 may control or facilitate transfer of data between one or more elements of computing system 1310, such as processor 1314, system memory 1316, communication interface 1322, display adapter 1326, input interface 1330, and storage interface 1334.

As illustrated in FIG. 12, computing system 1310 may also include at least one display device 1324 coupled to I/O controller 1320 via a display adapter 1326. Display device 1324 generally represents any type or form of device capable of visually displaying information forwarded by display adapter 1326. Similarly, display adapter 1326 generally represents any type or form of device configured to forward graphics, text, and other data from communication infrastructure 1312 (or from a frame buffer, as known in the art) for display on display device 1324.

As illustrated in FIG. 12, example computing system 1310 may also include at least one input device 1328 coupled to I/O controller 1320 via an input interface 1330. Input device 1328 generally represents any type or form of input device capable of providing input, either computer or human generated, to example computing system 1310. Examples of input device 1328 include, without limitation, a keyboard, a pointing device, a speech recognition device, variations or combinations of one or more of the same, and/or any other input device.

Additionally or alternatively, example computing system 1310 may include additional I/O devices. For example, example computing system 1310 may include I/O device 1336. In this example, I/O device 1336 may include and/or represent a user interface that facilitates human interaction with computing system 1310. Examples of I/O device 1336 include, without limitation, a computer mouse, a keyboard, a monitor, a printer, a modem, a camera, a scanner, a microphone, a touchscreen device, variations or combinations of one or more of the same, and/or any other I/O device.

Communication interface 1322 broadly represents any type or form of communication device or adapter capable of facilitating communication between example computing system 1310 and one or more additional devices. For example, in certain embodiments communication interface 1322 may facilitate communication between computing system 1310 and a private or public network including additional computing systems. Examples of communication interface 1322 include, without limitation, a wired network interface (such as a network interface card), a wireless network interface (such as a wireless network interface card), a modem, and any other suitable interface. In at least one embodiment, communication interface 1322 may provide a direct connection to a remote server via a direct link to a network, such as the Internet. Communication interface 1322 may also indirectly provide such a connection through, for example, a local area network (such as an Ethernet network), a personal area network, a telephone or cable network, a cellular telephone connection, a satellite data connection, or any other suitable connection.

In certain embodiments, communication interface 1322 may also represent a host adapter configured to facilitate communication between computing system 1310 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 1322 may also allow computing system 1310 to engage in distributed or remote computing. For example, communication interface 1322 may receive instructions from a remote device or send instructions to a remote device for execution.

In some examples, system memory 1316 may store and/or load a network communication program 1338 for execution by processor 1314. In one example, network communication program 1338 may include and/or represent software that enables computing system 1310 to establish a network connection 1342 with another computing system (not illustrated in FIG. 12) and/or communicate with the other computing system by way of communication interface 1322. In this example, network communication program 1338 may direct the flow of outgoing traffic that is sent to the other computing system via network connection 1342. Additionally or alternatively, network communication program 1338 may direct the processing of incoming traffic that is received from the other computing system via network connection 1342 in connection with processor 1314.

Although not illustrated in this way in FIG. 12, network communication program 1338 may alternatively be stored and/or loaded in communication interface 1322. For example, network communication program 1338 may include and/or represent at least a portion of software and/or firmware that is executed by a processor and/or Application Specific Integrated Circuit (ASIC) incorporated in communication interface 1322.

As illustrated in FIG. 12, example computing system 1310 may also include a primary storage device 1332 and a backup storage device 1333 coupled to communication infrastructure 1312 via a storage interface 1334. Storage devices 1332 and 1333 generally represent any type or form of storage device or medium capable of storing data and/or other computer-readable instructions. For example, storage devices 1332 and 1333 may be a magnetic disk drive (e.g., a so-called hard drive), a solid state drive, a floppy disk drive, a magnetic tape drive, an optical disk drive, a flash drive, or the like. Storage interface 1334 generally represents any type or form of interface or device for transferring data between storage devices 1332 and 1333 and other components of computing system 1310.

In certain embodiments, storage devices 1332 and 1333 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 1332 and 1333 may also include other similar structures or devices for allowing computer software, data, or other computer-readable instructions to be loaded into computing system 1310. For example, storage devices 1332 and 1333 may be configured to read and write software, data, or other computer-readable information. Storage devices 1332 and 1333 may also be a part of computing system 1310 or may be a separate device accessed through other interface systems.

Many other devices or subsystems may be connected to computing system 1310. Conversely, all of the components and devices illustrated in FIG. 12 need not be present to practice the embodiments described and/or illustrated herein. The devices and subsystems referenced above may also be interconnected in different ways from that shown in FIG. 12. Computing system 1310 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium.

The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 1310. All or a portion of the computer program stored on the computer-readable medium may then be stored in system memory 1316 and/or various portions of storage devices 1332 and 1333. When executed by processor 1314, a computer program loaded into computing system 1310 may cause processor 1314 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 1310 may be configured as an Application Specific Integrated Circuit (ASIC) adapted to implement one or more of the example embodiments disclosed herein.

FIG. 13 is a block diagram of an example network architecture 1400 in which client systems 1410, 1420, and 1430 and servers 1440 and 1445 may be coupled to a network 1450. As detailed above, all or a portion of network architecture 1400 may perform and/or be a means for performing, either alone or in combination with other elements, one or more of the steps disclosed herein (such as one or more of the steps illustrated in FIG. 4-11). All or a portion of network architecture 1400 may also be used to perform and/or be a means for performing other steps and features set forth in the instant disclosure.

Client systems 1410, 1420, and 1430 generally represent any type or form of computing device or system, such as example computing system 1310 in FIG. 12. Similarly, servers 1440 and 1445 generally represent computing devices or systems, such as application servers or database servers, configured to provide various database services and/or run certain software applications. Network 1450 generally represents any telecommunication or computer network including, for example, an intranet, a WAN, a LAN, a PAN, or the Internet. In one example, client systems 1410, 1420, and/or 1430 and/or servers 1440 and/or 1445 may include all or a portion of system 500 from FIG. 5.

As illustrated in FIG. 13, one or more storage devices 1460(1)-(N) may be directly attached to server 1440. Similarly, one or more storage devices 1470(1)-(N) may be directly attached to server 1445. Storage devices 1460(1)-(N) and storage devices 1470(1)-(N) generally represent any type or form of storage device or medium capable of storing data and/or other computer-readable instructions. In certain embodiments, storage devices 1460(1)-(N) and storage devices 1470(1)-(N) may represent Network-Attached Storage (NAS) devices configured to communicate with servers 1440 and 1445 using various protocols, such as Network File System (NFS), Server Message Block (SMB), or Common Internet File System (CIFS).

Servers 1440 and 1445 may also be connected to a Storage Area Network (SAN) fabric 1480. SAN fabric 1480 generally represents any type or form of computer network or architecture capable of facilitating communication between a plurality of storage devices. SAN fabric 1480 may facilitate communication between servers 1440 and 1445 and a plurality of storage devices 1490(1)-(N) and/or an intelligent storage array 1495. SAN fabric 1480 may also facilitate, via network 1450 and servers 1440 and 1445, communication between client systems 1410, 1420, and 1430 and storage devices 1490(1)-(N) and/or intelligent storage array 1495 in such a manner that devices 1490(1)-(N) and array 1495 appear as locally attached devices to client systems 1410, 1420, and 1430. As with storage devices 1460(1)-(N) and storage devices 1470(1)-(N), storage devices 1490(1)-(N) and intelligent storage array 1495 generally represent any type or form of storage device or medium capable of storing data and/or other computer-readable instructions.

In certain embodiments, and with reference to example computing system 1310 of FIG. 12, a communication interface, such as communication interface 1322 in FIG. 12, may be used to provide connectivity between each client system 1410, 1420, and 1430 and network 1450. Client systems 1410, 1420, and 1430 may be able to access information on server 1440 or 1445 using, for example, a web browser or other client software. Such software may allow client systems 1410, 1420, and 1430 to access data hosted by server 1440, server 1445, storage devices 1460(1)-(N), storage devices 1470(1)-(N), storage devices 1490(1)-(N), or intelligent storage array 1495. Although FIG. 12 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 1440, server 1445, storage devices 1460(1)-(N), storage devices 1470(1)-(N), storage devices 1490(1)-(N), intelligent storage array 1495, or any combination thereof. All or a portion of one or more of the example embodiments disclosed herein may also be encoded as a computer program, stored in server 1440, run by server 1445, and distributed to client systems 1410, 1420, and 1430 over network 1450.

As detailed above, computing system 1310 and/or one or more components of network architecture 1400 may perform and/or be a means for performing, either alone or in combination with other elements, one or more steps of an example method for virtual care.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of the example systems disclosed herein may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example systems disclosed herein may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example systems disclosed herein may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example systems disclosed herein may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example systems disclosed herein may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example systems disclosed herein may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein.

Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A system for treating food traps, the system comprising: an intraoral scanner;

a processor coupled in electronic communication with the intraoral scanner; and memory comprising instructions that when executed by the processor cause the system to carry out a method comprising: receiving a 3D digital model of a patient's detention; analyzing the 3D digital model of the patient's detention by detecting anatomic structures in the 3D digital model of the patient's detention that correspond to food traps; displaying the 3D digital model of the patient's detention on a display; providing digital feedback on the displayed 3D digital model of the patient's detention that identifies a location of the food traps; and generating a treatment plan for treating the food traps.

Clause 2. The system of clause 1, wherein: receiving the 3D digital model of the patient's dentition includes scanning the patient's detention with a 3D intraoral scanner, and wherein the 3D digital model is a 3D surface model.

Clause 3. The system of clause 1, wherein: receiving the 3D digital model of the patient's dentition includes scanning the patient's detention with a multi-modal 3D intraoral scanner, and wherein the 3D digital model is a 3D surface and volumetric model.

Clause 4. The system of clause 3, wherein: the 3D model includes near infrared subsurface data or CBCT data.

Clause 5. The system of clause 1, wherein: analyzing the 3D digital model of the patient's detention by detecting anatomic structures includes detecting apertures between adjacent teeth that extend from a buccal side to a lingual side of the adjacent teeth.

Clause 6. The system of clause 1, wherein: analyzing the 3D digital model of the patient's detention by detecting anatomic structures includes detecting recession of the patient's dentition to form an aperture between adjacent teeth that extend from a buccal side to a lingual side of the adjacent teeth.

Clause 7. The system of clause 1, wherein: analyzing the 3D digital model of the patient's detention by detecting anatomic structures includes detecting recession of interdental papilla to form an aperture between adjacent teeth that extend from a buccal side to a lingual side of the adjacent teeth.

Clause 8. The system of clause 1, wherein: analyzing the 3D digital model of the patient's detention by detecting anatomic structures includes detecting an undercut at a base of a crown of at least one tooth.

Clause 9. The system of clause 1, wherein: analyzing the 3D digital model of the patient's detention by detecting anatomic structures includes detecting an undercut in at least one tooth proximate gingiva of the patient's detention.

Clause 10. The system of clause 1, wherein: analyzing the 3D digital model of the patient's detention by detecting anatomic structures includes detecting an undercut in at least one tooth proximate gingiva of the patient's detention.

Clause 11. The system of clause 1, wherein: analyzing the 3D digital model of the patient's detention by detecting anatomic structures includes detecting a gap between a tooth and gingiva.

Clause 12. The system of clause 1, wherein: analyzing the 3D digital model of the patient's detention by detecting anatomic structures includes detecting a teeth that overlap each other in a buccal-lingual direction.

Clause 13. The system of clause 1, wherein: receiving the 3D digital model of the patient's dentition includes receiving a first 3D digital model of the patient's detention in normal occlusion and a second 3D digital model of the patient's detention in bite occlusion with bite forces applied; and analyzing the 3D digital model of the patient's detention by detecting anatomic structures includes detecting an aperture in an interproximal region between adjacent teeth in the second model that is larger than the aperture in the interproximal region between the adjacent teeth in the first model.

Clause 14. The system of clause 1, wherein: wherein the feedback includes highlighting a region of the 3D model that includes the food trap.

Clause 15. The system of clause 1, wherein: wherein the feedback includes modifying a color of a region of the 3D model that includes the food trap.

Clause 16. The system of clause 1, wherein: wherein the feedback includes modifying a generated perimeter around a region of the 3D model that includes the food trap.

Clause 17. The system of clause 1, wherein: wherein generating the treatment plan for treating the food traps includes generating an orthodontic treatment plan to move teeth of the patient's dentition from a first arrangement with the food trap to a second arrangement without the food trap.

Clause 18. A system for treating food traps, the system comprising: a processor; and memory comprising instructions that when executed by the processor cause the system to carry out a method of: receiving a plurality of 3D digital models of a patient's detention taken over time; analyzing the plurality of 3D digital models of the patient's detention by detecting changes in anatomic structures between each of the plurality of 3D digital models of the patient's detention; determining that the detected changes indicate a formation of a food trap; displaying the 3D digital model of the patient's detention on a display; and providing digital feedback on the displayed 3D digital model of the patient's detention that identifies a location of the formation of the food trap.

Clause 19. The system of clause 18, wherein: determining that the detected changes indicate a formation of a food trap includes extrapolating future tooth movement based on the plurality of 3D digital models; and the memory further comprises instructions that when executed by the processor cause the system to carry out the method, the method further comprising: generating a treatment plan for treating the formation of the food traps, the treatment plan including moving teeth of the patient's dentition from a first arrangement to a second arrangement that avoids the extrapolated future tooth movement.

Clause 20. The system of clause 18, wherein: the memory further comprises instructions that when executed by the processor cause the system to carry out the method, the method further comprising: generating a treatment plan for treating the formation of the food traps, the treatment plan to halt or reverse gingiva recession detected in the plurality of 3D digital models.

Clause 21. A system for treating food traps, the system comprising: a processor; and memory comprising instructions that when executed by the processor cause the system to carry out a method of: receiving a 3D digital model of a patient's detention; analyzing the 3D digital model of the patient's detention by detecting anatomic structures in the 3D digital model of the patient's detention that correspond to food traps; displaying the 3D digital model of the patient's detention on a display; and providing digital feedback on the displayed 3D digital model of the patient's detention that identifies a location of the food traps.

Clause 22. The system of clause 21, wherein: the memory further comprises instructions that when executed by the processor cause the system to carry out the method, the method further comprising: generating a treatment plan for treating the food traps; receiving dental feedback on the treatment plan, wherein the dental feedback includes a change in a position of one or more teeth of the patient's dentition in a final arrangement; and analyzing the dental feedback by detecting anatomic structures in the 3D digital model of the patient's detention that correspond to food traps.

Clause 23. The system of clause 22, wherein: analyzing the dental feedback includes detecting anatomic structures in a final arrangement that correspond to food traps.

Clause 24. The system of clause 21, wherein: the memory further comprises instructions that when executed by the processor cause the system to carry out the method, the method further comprising: generating a treatment plan for treating the food traps; receiving dental feedback on the treatment plan, wherein the dental feedback includes a change in a shape, position, or orientation of one or more prosthetics; and analyzing the dental feedback by detecting anatomic structures in the 3D digital model of the patient's detention that correspond to food traps.

Clause 25. The system of clause 24, wherein: analyzing the dental feedback includes detecting anatomic or prosthetic structures that correspond to food traps.

Clause 26. A method for treating food traps, the method comprising: receiving a 3D digital model of a patient's detention; analyzing the 3D digital model of the patient's detention by detecting anatomic structures in the 3D digital model of the patient's detention that correspond to food traps; displaying the 3D digital model of the patient's detention on a display; providing digital feedback on the displayed 3D digital model of the patient's detention that identifies a location of the food traps; and generating a treatment plan for treating the food traps.

Clause 27. The method of clause 26, wherein: receiving the 3D digital model of the patient's dentition includes scanning the patient's detention with a 3D intraoral scanner, and wherein the 3D digital model is a 3D surface model.

Clause 28. The method of clause 26, wherein: receiving the 3D digital model of the patient's dentition includes scanning the patient's detention with a multi-modal 3D intraoral scanner, and wherein the 3D digital model is a 3D surface and volumetric model.

Clause 29. The method of clause 28, wherein: the 3D model includes near infrared subsurface data or CBCT data.

Clause 30. The method of clause 26, wherein: analyzing the 3D digital model of the patient's detention by detecting anatomic structures includes detecting apertures between adjacent teeth that extend from a buccal side to a lingual side of the adjacent teeth.

Clause 31. The method of clause 26, wherein: analyzing the 3D digital model of the patient's detention by detecting anatomic structures includes detecting recession of the patient's dentition to form an aperture between adjacent teeth that extend from a buccal side to a lingual side of the patient's teeth.

Clause 32. The method of clause 26, wherein: analyzing the 3D digital model of the patient's detention by detecting anatomic structures includes detecting recession of interdental papilla to form an aperture between adjacent teeth that extend from a buccal side to a lingual side of the patient's teeth.

Clause 33. The method of clause 26, wherein: analyzing the 3D digital model of the patient's detention by detecting anatomic structures includes detecting an undercut in the patient's teeth at a base of a crown of the patient's teeth.

Clause 34. The method of clause 26, wherein: analyzing the 3D digital model of the patient's detention by detecting anatomic structures includes detecting an undercut in at least one tooth proximate gingiva of the patient's detention.

Clause 35. The method of clause 26, wherein: analyzing the 3D digital model of the patient's detention by detecting anatomic structures includes detecting an undercut in at least one tooth proximate gingiva of the patient's detention.

Clause 36. The method of clause 26, wherein: analyzing the 3D digital model of the patient's detention by detecting anatomic structures includes detecting a gap between a tooth and gingiva.

Clause 37. The method of clause 26, wherein: analyzing the 3D digital model of the patient's detention by detecting anatomic structures includes detecting a teeth that overlap each other in a buccal-lingual direction.

Clause 38. The method of clause 26, wherein: receiving the 3D digital model of the patient's dentition includes receiving a first 3D digital model of the patient's detention in normal occlusion and a second 3D digital model of the patients detention in bite occlusion with bite forces applied; and analyzing the 3D digital model of the patient's detention by detecting anatomic structures includes detecting an aperture in an interproximal region between adjacent teeth in the second model that is larger than the aperture in the interproximal region between the adjacent teeth in the first model.

Clause 39. The method of clause 26, wherein: wherein the feedback includes highlighting a region of the 3D model that includes the food trap.

Clause 40. The method of clause 26, wherein: wherein the feedback includes modifying a color a region of the 3D model that includes the food trap.

Clause 41. The method of clause 26, wherein: wherein the feedback includes modifying a generating a perimeter around a region of the 3D model that includes the food trap.

Clause 42. The method of clause 26, wherein: wherein generating the treatment plan for treating the food traps includes generating an orthodontic treatment plan to move the patient's teeth from a first arrangement with the food trap to a second arrangement without the food trap.

Clause 43. A method for treating food traps, the method comprising: receiving a plurality of 3D digital models of a patient's detention taken over time; analyzing the plurality of 3D digital models of the patient's detention by detecting changes in anatomic structures between each of the plurality of 3D digital models of the patient's detention; determining that the detected changes indicate a formation of a food trap; displaying the 3D digital model of the patient's detention on a display; providing digital feedback on the displayed 3D digital model of the patient's detention that identifies a location of the formation of the food trap; and generating a treatment plan for treating the formation of the food traps.

Clause 44. The method of clause 43, wherein: wherein determining that the detected changes indicate a formation of a food trap includes extrapolating future tooth movement based on the plurality of 3D digital models; generating the treatment plan for treating the food traps includes generating an orthodontic treatment plan to move the patient's teeth from a first arrangement to a second arrangement that avoids the extrapolated future tooth movement.

Clause 45. The method of clause 43, wherein: generating a treatment plan for treating the formation of the food traps includes generating a treatment plan to halt or reverse gingiva recession detected in the plurality of 3D digital models.

Clause 46. A method for treating food traps, the method comprising: receiving a 3D digital model of a patient's detention; analyzing the 3D digital model of the patient's detention by detecting anatomic structures in the 3D digital model of the patient's detention that correspond to food traps; displaying the 3D digital model of the patient's detention on a display; providing digital feedback on the displayed 3D digital model of the patient's detention that identifies a location of the food traps; generating a treatment plan for treating the food traps; receiving dental feedback on the treatment plan; analyzing the dental feedback by detecting anatomic structures in the 3D digital model of the patient's detention that correspond to food traps.

Clause 47. The method of clause 46, wherein: the dental feedback includes a change in a position of one or more of the patient's teeth in a final arrangement.

Clause 48. The method of clause 47, wherein: analyzing the dental feedback includes detecting anatomic structures in a final arrangement that correspond to food traps.

Clause 49. The method of clause 46, wherein: the dental feedback includes a change in a shape, position, or orientation of one or more prosthetics.

Clause 50. The method of clause 47, wherein: analyzing the dental feedback includes detecting anatomic or prosthetic structures that correspond to food traps.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system for treating food traps, the system comprising:

a processor; and memory comprising instructions that when executed by the processor cause the system to carry out a method of:

receiving a plurality of 3D digital models of a patient's detention taken over time;

analyzing the plurality of 3D digital models of the patient's detention by detecting changes in anatomic structures between each of the plurality of 3D digital models of the patient's detention;

determining that the detected changes indicate a formation of a food trap between the anatomic structures;

displaying the 3D digital model of the patient's detention on a display; and providing digital feedback on the displayed 3D digital model of the patient's detention that identifies a location of the formation of the food trap.

2. The system of claim 1, wherein:

determining that the detected changes indicate a formation of a food trap includes extrapolating future tooth movement based on the plurality of 3D digital models; and the memory further comprises instructions that when executed by the processor cause the system to carry out the method, the method further comprising:

generating a treatment plan for treating the formation of the food traps, the treatment plan including moving teeth of the patient's dentition from a first arrangement to a second arrangement that avoids the extrapolated future tooth movement.

3. The system of claim 1, wherein:

the memory further comprises instructions that when executed by the processor cause the system to carry out the method, the method further comprising:

generating a treatment plan for treating the formation of the food traps, the treatment plan to halt or reverse gingiva recession detected in the plurality of 3D digital models.

4. A system for treating food traps, the system comprising:

an intraoral scanner;

a processor coupled in electronic communication with the intraoral scanner; and memory comprising instructions that when executed by the processor cause the system to carry out a method comprising:

receiving a 3D digital model of a patient's detention;

analyzing the 3D digital model of the patient's detention by detecting food traps between anatomic structures in the 3D digital model of the patient's detention;

displaying the 3D digital model of the patient's detention on a display; and providing digital feedback on the displayed 3D digital model of the patient's detention that identifies a location of the food traps.

5. The system of claim 4, wherein:

receiving the 3D digital model of the patient's dentition includes scanning the patient's detention with a 3D intraoral scanner, and wherein the 3D digital model is a 3D surface model.

6. The system of claim 4, wherein:

receiving the 3D digital model of the patient's dentition includes scanning the patient's detention with a multi-modal 3D intraoral scanner, and wherein the 3D digital model is a 3D surface and volumetric model.

7. The system of claim 6, wherein:
the 3D model includes near infrared subsurface data or CBCT data.

8. The system of claim 4, wherein:
analyzing the 3D digital model of the patient's detention by detecting anatomic structures includes detecting apertures between adjacent teeth that extend from a buccal side to a lingual side of the adjacent teeth.

9. The system of claim 4, wherein:
analyzing the 3D digital model of the patient's detention by detecting anatomic structures includes detecting recession of the patient's dentition to form an aperture between adjacent teeth that extend from a buccal side to a lingual side of the adjacent teeth.

10. The system of claim 4, wherein:
analyzing the 3D digital model of the patient's detention by detecting anatomic structures includes detecting recession of interdental papilla to form an aperture between adjacent teeth that extend from a buccal side to a lingual side of the adjacent teeth.

11. The system of claim 4, wherein:
analyzing the 3D digital model of the patient's detention by detecting anatomic structures includes detecting an undercut at a base of a crown of at least one tooth.

12. The system of claim 4, wherein:
analyzing the 3D digital model of the patient's detention by detecting anatomic structures includes detecting an undercut in at least one tooth proximate gingiva of the patient's detention.

13. The system of claim 4, wherein:
analyzing the 3D digital model of the patient's detention by detecting anatomic structures includes detecting an undercut in at least one tooth proximate gingiva of the patient's detention.

14. The system of claim 4, wherein:
analyzing the 3D digital model of the patient's detention by detecting anatomic structures includes detecting a gap between a tooth and gingiva.

15. The system of claim 4, wherein:
analyzing the 3D digital model of the patient's detention by detecting anatomic structures includes detecting a teeth that overlap each other in a buccal-lingual direction.

16. The system of claim 4, wherein:
receiving the 3D digital model of the patient's dentition includes receiving a first 3D digital model of the patient's detention in normal occlusion and a second 3D digital model of the patient's detention in bite occlusion with bite forces applied; and
analyzing the 3D digital model of the patient's detention by detecting anatomic structures includes detecting an aperture in an interproximal region between adjacent teeth in the second model that is larger than the aperture in the interproximal region between the adjacent teeth in the first model.

17. The system of claim 4, wherein:
wherein the feedback includes highlighting a region of the 3D model that includes the food trap.

18. The system of claim 4, wherein:
wherein the feedback includes modifying a color of a region of the 3D model that includes the food trap.

19. The system of claim 4, wherein:
wherein the feedback includes modifying a generated perimeter around a region of the 3D model that includes the food trap.

20. The system of claim 4, wherein:
the method further comprises generating a treatment plan for treating the food traps by generating an orthodontic treatment plan to move teeth of the patient's dentition from a first arrangement with the food trap to a second arrangement without the food trap.

21. A system for treating food traps, the system comprising:
a processor; and
memory comprising instructions that when executed by the processor cause the system to carry out a method of:
receiving a 3D digital model of a patient's detention;
analyzing the 3D digital model of the patient's detention by detecting food traps between anatomic structures in the 3D digital model of the patient's detention;
displaying the 3D digital model of the patient's detention on a display; and
providing digital feedback on the displayed 3D digital model of the patient's detention that identifies a location of the food traps.

22. The system of claim 21, wherein:
the memory further comprises instructions that when executed by the processor cause the system to carry out the method, the method further comprising:
generating a treatment plan for treating the food traps;
receiving dental feedback on the treatment plan, wherein the dental feedback includes a change in a position of one or more teeth of the patient's dentition in a final arrangement; and
analyzing the dental feedback by detecting anatomic structures in the 3D digital model of the patient's detention that correspond to food traps.

23. The system of claim 22, wherein:
analyzing the dental feedback includes detecting anatomic structures in a final arrangement that correspond to food traps.

24. The system of claim 21, wherein:
the memory further comprises instructions that when executed by the processor cause the system to carry out the method, the method further comprising:
generating a treatment plan for treating the food traps;
receiving dental feedback on the treatment plan, wherein the dental feedback includes a change in a shape, position, or orientation of one or more prosthetics; and
analyzing the dental feedback by detecting anatomic structures in the 3D digital model of the patient's detention that correspond to food traps.

25. The system of claim 24, wherein:
analyzing the dental feedback includes detecting anatomic or prosthetic structures that correspond to food traps.

* * * * *